(12) United States Patent
Chacón et al.

(10) Patent No.: US 11,710,234 B2
(45) Date of Patent: Jul. 25, 2023

(54) SYSTEMS AND METHODS OF MONITORING MEDICAL IMPLANTS

(71) Applicant: Establishment Labs S.A., Alajuela (CR)

(72) Inventors: Manuel Chacón, Alajuela (CR); Allan Orozco, Alajuela (CR); David Meléndez, Alajuela (CR); Nabil Vindas, Alajuela (CR); Yamil Vindas, Alajuela (CR); Juan José Chacón Quirós, Alajuela (CR)

(73) Assignee: Establishment Labs S.A., Alajuela (CR)

(*) Notice: Subject to any disclaimer, the term of this patent is extended or adjusted under 35 U.S.C. 154(b) by 638 days.

(21) Appl. No.: 16/591,011

(22) Filed: Oct. 2, 2019

(65) Prior Publication Data

US 2020/0111213 A1    Apr. 9, 2020

Related U.S. Application Data

(60) Provisional application No. 62/740,818, filed on Oct. 3, 2018.

(51) Int. Cl.
| | |
|---|---|
| *G06T 7/00* | (2017.01) |
| *A61B 8/08* | (2006.01) |
| *A61B 8/00* | (2006.01) |
| *A61F 2/12* | (2006.01) |
| *A61B 5/00* | (2006.01) |

(52) U.S. Cl.
CPC .......... *G06T 7/0014* (2013.01); *A61B 8/0841* (2013.01); *A61B 8/461* (2013.01); *A61B 8/5223* (2013.01); *A61B 8/5269* (2013.01); *A61F 2/12* (2013.01); *A61B 5/4851* (2013.01); *G06T 2207/10132* (2013.01); *G06T 2207/20084* (2013.01); *G06T 2207/30068* (2013.01)

(58) Field of Classification Search
CPC ......... G06T 7/0014; G06T 2207/10132; G06T 2207/20084; G06T 2207/30068; A61B 8/0841; A61B 8/461; A61B 8/5223; A61B 8/5269; A61B 5/4851; A61F 2/12
See application file for complete search history.

(56) References Cited

U.S. PATENT DOCUMENTS

| | | | | |
|---|---|---|---|---|
| 2011/0299754 A1* | 12/2011 | Suri | ...................... | G06T 7/0012 |
| | | | | 382/131 |
| 2021/0244856 A1* | 8/2021 | Govreen-Segal | ....... | A61L 27/48 |
| 2022/0015742 A1* | 1/2022 | Grover | ................... | A61B 8/469 |

* cited by examiner

*Primary Examiner* — Vu Le
*Assistant Examiner* — Winta Gebreslassie
(74) *Attorney, Agent, or Firm* — Schwegman Lundberg & Woessner, P.A.

(57) ABSTRACT

Methods of processing images, such as ultrasound images, to determine integrity of an implant are described. The method may include receiving an ultrasound image of an implant in a body of a subject; determining one or more characteristics of a surface of the implant based on an intensity of pixels of the ultrasound image; generating a predicted status of the implant based on the one or more characteristics by comparison of the one or more characteristics with a database of image data; and displaying the predicted status of the implant. The implant may be a breast implant, for example, wherein the method is useful for analyzing the presence or probability of extracapsular ruptures, contractures, and combinations thereof.

20 Claims, 24 Drawing Sheets

FIG. 14B

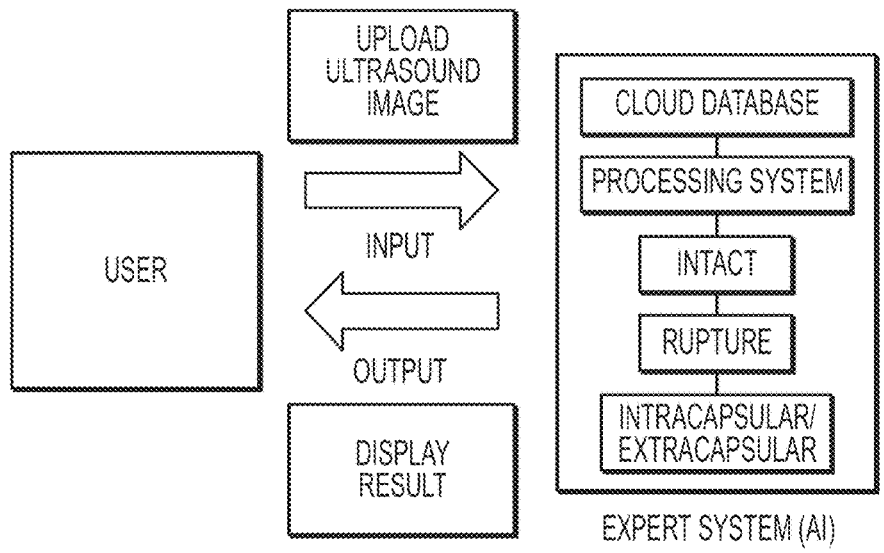
FIG. 19
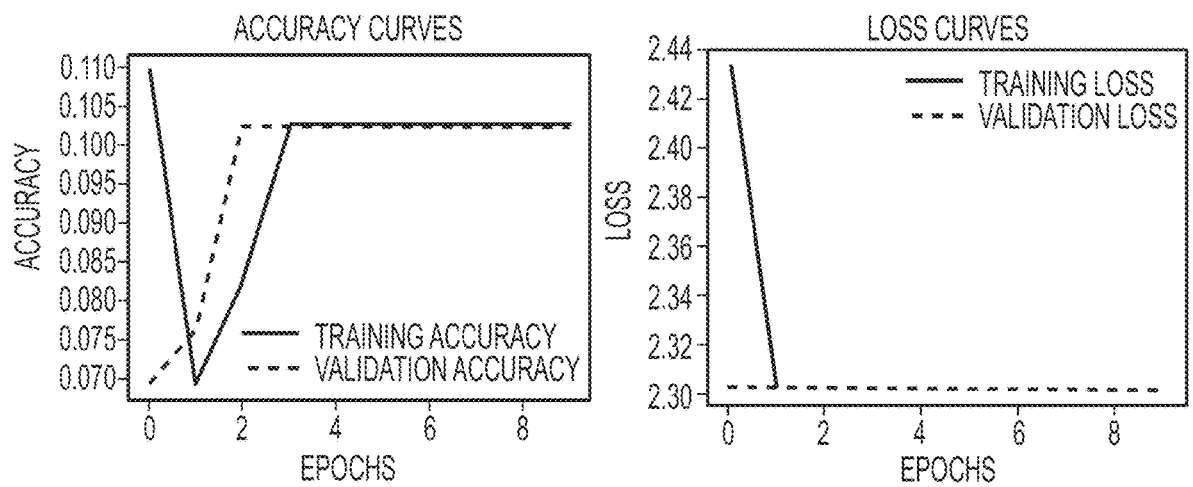
FIG. 20A  FIG. 20B

| Layer (type) | Output Shape | Param # |
|---|---|---|
| dense_1 (Dense) | (None, 80) | 9216080 |
| dropout_1 (Dropout) | (None, 80) | 0 |
| dense_2 (Dense) | (None, 3) | 243 |

Total params: 9,216,323
Trainable params: 9,216,323
Non-trainable params: 0

FIG. 22B

SYSTEMS AND METHODS OF MONITORING MEDICAL IMPLANTS

CROSS-REFERENCE TO RELATED APPLICATIONS

This application claims priority to U.S. Provisional Application No. 62/740,818 filed on Oct. 3, 2018, which is incorporated by reference herein in its entirety.

TECHNICAL FIELD

Embodiments of the present disclosure relate generally to systems and methods for assessing medical implants over time. More specifically, the present disclosure relates to systems and a methods for monitoring the status of an implant via image processing, e.g., to screen for ruptures or other abnormalities of medical implants in a body of a patient.

BACKGROUND

Medical implants are useful for a variety of medical procedures, from reconstructive to aesthetic surgeries. In some cases, the implant includes a gel or fluid to simulate natural tissue or to allow for selective expansion and retraction of the implant volume. Such examples include, e.g., breast implants, tissue expanders, and other medical implants used as prosthesis in various aesthetic and reconstructive procedures. Implant ruptures can have various causes. Many ruptures have no discernable traumatic origin and can occur in asymptomatic patients. The incidence of rupture typically increases with implant age. The possibility of a rupture or other failure of the implant is of concern due to the difficulty in monitoring the integrity of the implant over time, in a non-invasive manner. Ruptures may also be iatrogenic in nature, i.e. caused by an inadvertent action during the implantation procedure. Such actions may result in an abrasion or "nick" (a shallow notch, cut or indentation on the shell of the implant) that results in a weakness in the surface leading to a longer term rupture. Such actions may inadvertently occur during the packaging or insertion process.

Implants that include a liquid or gel filler material may deteriorate over time and become more prone to rupturing. Patients may require additional surgeries due to complications with the placement of an implant and/or an implant failure, which may occur soon after implantation or unexpectedly at some point in the future. Implants may rupture for a number of reasons, such as excessive pressure applied to the implant, damage occurring during a surgical procedure, shifting or rotating in a patient's body, folding or wrinkling of the implant's shell, among other reasons. In some cases, an implant may fail without rupturing. For example, a gel bleed refers to a filler material, such as silicone, e.g., microscopic silicone leaking through an intact implant shell. This type of failure is typically related to the chemical affinity between the outer shell of, for example, a silicone elastomer, and the filler, such as silicone, contained therein. The filler, if in contact with the outer shell, can break the noncovalent molecular bonds between the polymer chains, causing swelling and weakening of the shell itself. Once a filler separates from its shell, the filler can migrate within a patient's body and cause health problems.

Current methods for detecting implant failures, such as ruptures, include magnetic resonance imaging (MM). Patients are often advised to have MM scans to ensure their implants have not ruptured or otherwise failed. Medical professionals may examine images from an MRI scan of the patient in order to diagnose implant failures. However, MM imaging is time consuming, expensive, and relies on the medical professional's analysis of the image. Moreover, some patients are unable to undergo MRI scans, e.g., due to metallic implants or other metallic materials present in the body.

SUMMARY

The present disclosure discusses systems and methods of using ultrasound to monitor implants and detect implant failures, among other aspects. Embodiments of the present disclosure relate to, among other things, systems and methods for assessing the status of a medical device implanted in a patient. For example, aspects of the present disclosure relate to implant monitoring and rupture detection, e.g., to provide guidance for medical professionals in diagnosing possible complications associated with medical implants.

In some aspects, complications associated with medical implants may be detected using one or more ultrasound devices. In some examples, the disclosed systems and methods may detect implant failures or other aspects of medical implants by analyzing ultrasound images using artificial intelligence, such as by using electronic neural networks. Artificial neural networks includes computing systems that may "learn" to perform tasks by considering examples, such as samples of ultrasound images.

The methods herein include use of artificial neural networks, which may learn to recognize various features in ultrasound images that are indicative of ruptured medical implants. In order to train an artificial intelligence system, a dataset of images may be used. For example, such networks may analyze sample images of medical implants (e.g., optionally stored in a database), wherein each image is associated with a rupture or does not include a rupture. For example, each sample image provided to the network may be associated with a label such as "including a rupture" or "not including a rupture," wherein the label may be assigned and/or verified manually. These labeled images then may be used by the network to identify ruptures in other images, e.g., having similar characteristics.

Ultrasound images of actual implant ruptures, and images that represent different types of defects observed in patients may be limited. Accordingly, in some examples, at least a portion of the images, or all of the images, of a database of images accessed by an artificial neural network may be created artificially by using mathematical models that simulate features characteristic of implants with and without ruptures. With a dataset of images of medical implants, the artificial intelligence system, such as an artificial neural network, may be trained so that the system may analyze and identify irregularities and abnormalities in real images of medical implants to help identify, diagnose, and/or resolve medical complications.

The present disclosure includes a computer-implemented method of processing images to determine integrity of an implant, the method comprising receiving, e.g., by a computer, an ultrasound image of an implant in a body of a subject; determining, e.g., via a processor, one or more characteristics of a surface of the implant based on an intensity of pixels of the ultrasound image, e.g., according to a greyscale range; generating, e.g., by the processor, a predicted status of the implant based on the one or more characteristics by comparison of the one or more characteristics with a database of image data; and displaying the predicted status of the implant. The implant may be a breast implant or a tissue expander, for example.

Each of the embodiments disclosed herein may include one or more of the features described in connection with any of the other disclosed embodiments. It is understood that the foregoing general description and the following detailed description are exemplary and explanatory only and are not restrictive of the present disclosure. The database of image data may include a plurality of breast implant ultrasound images exhibiting extracapsular ruptures, contractures, and combinations thereof. In some aspects, the database of image data includes at least 50,000 images. The database of image data may include simulated images, real images, or both, which may exhibit echo lines, a snowstorm feature, or a combination thereof, e.g., as an indication of an irregularity of an implant. Determining the one or more characteristics may include determining a spatial period of consecutive echogenic lines. Further, for example, determining the one or more characteristics may include calculating a change in the intensity of pixels in a vertical direction of the ultrasound image. Determining the one or more characteristics may include identifying echo lines, a snowstorm feature, or a combination thereof in the ultrasound image. In at least one example, determining the one or more characteristics includes distinguishing a snowstorm indicative of extracapsular rupture from a noise snowstorm. The method may further comprise calculating a probability of implant failure based on the determined one or more characteristics, and optionally displaying the predicted status of the implant includes displaying the probability. Generating the predicted status of the implant may be performed by an artificial neural network.

The present disclosure also includes system for processing images to determine integrity of an implant. For example, the system may comprise at least one data storage device storing instructions processing images to determine integrity of an implant; and at least one processor configured to execute the instructions to perform a method as described above and/or elsewhere herein. For example, the processor may be configured to execute instructions to perform a method comprising: receiving an ultrasound image of an implant in a body of a subject; determining one or more characteristics of a surface of the implant based on a greyscale intensity of pixels of the ultrasound image; generating a predicted status of the implant based on the one or more characteristics by comparison of the one or more characteristics with a database of image data; and displaying the predicted status of the implant, e.g., on a display. The at least one data storage device of the system may comprise the database of image data. For example, the database of image data may include at least 50,000 images. In at least one example, the database of image data includes simulated images and/or real images exhibiting echo lines, a snowstorm feature, or a combination thereof. The database of image data may include a plurality of breast implant ultrasound images exhibiting extracapsular ruptures, contractures, and combinations thereof.

The present disclosure further includes a non-transitory computer-readable medium storing instructions that, when executed by a processor, cause the processor to perform a method for processing images to determine integrity of an implant. Such a method may include: receiving an ultrasound image of an implant in a body of a subject; determining one or more characteristics of a surface of the implant based on a greyscale intensity of pixels of the ultrasound image; generating a predicted status of the implant based on the one or more characteristics by comparison of the one or more characteristics with a database of image data; and displaying the predicted status of the implant, e.g., on a display. Determining the one or more characteristics may include calculating a change in the greyscale intensity of pixels in a vertical direction of the ultrasound image. Additionally or alternatively, determining the one or more characteristics may include distinguishing a snowstorm indicative of extracapsular rupture from a noise snowstorm. The method may further comprise calculating a probability of implant failure based on the determined one or more characteristics.

It is to be understood that both the foregoing general description and the following detailed description are exemplary and explanatory only and are not restrictive of the present disclosure.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

Figure 14B:
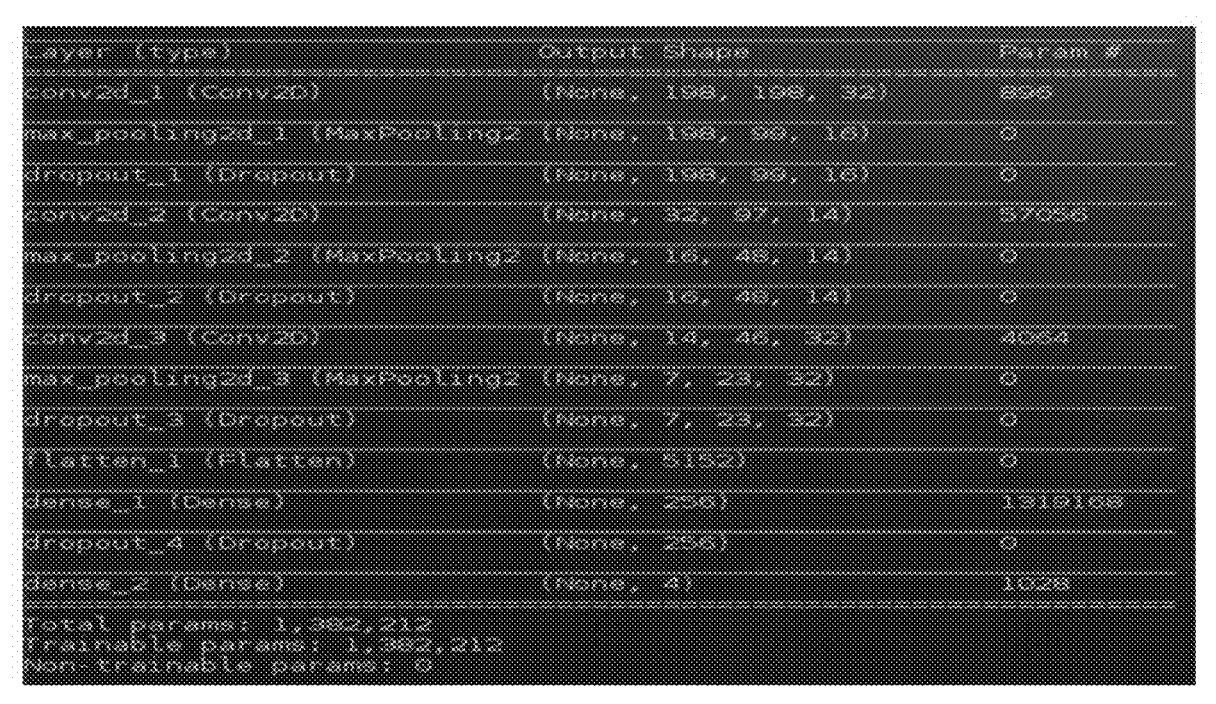

FIGS. 14A and 14B illustrate an artificial intelligence architecture, according to some aspects of the present disclosure.

FIG. 19 illustrates a system architecture, according to some aspects of the present disclosure.

FIGS. 20A-20B and 21A-21B illustrate training accuracy, validation accuracy, training loss, and validation loss curves for an artificial intelligence system, according to some aspects of the present disclosure.

FIGS. 22A and 22B illustrate an artificial intelligence architecture, according to some aspects of the present disclosure.

DETAILED DESCRIPTION

Figure 1A:
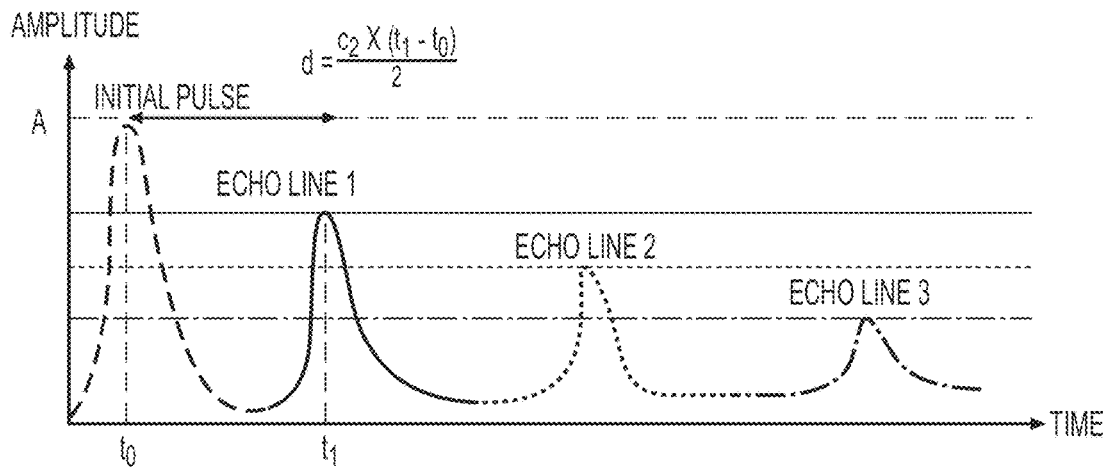
FIG. 1A illustrates a graph of amplitude versus time of a measured sound wave, and FIG. 1B describes related environments, according to some aspects of the present disclosure.
Figure 1B:
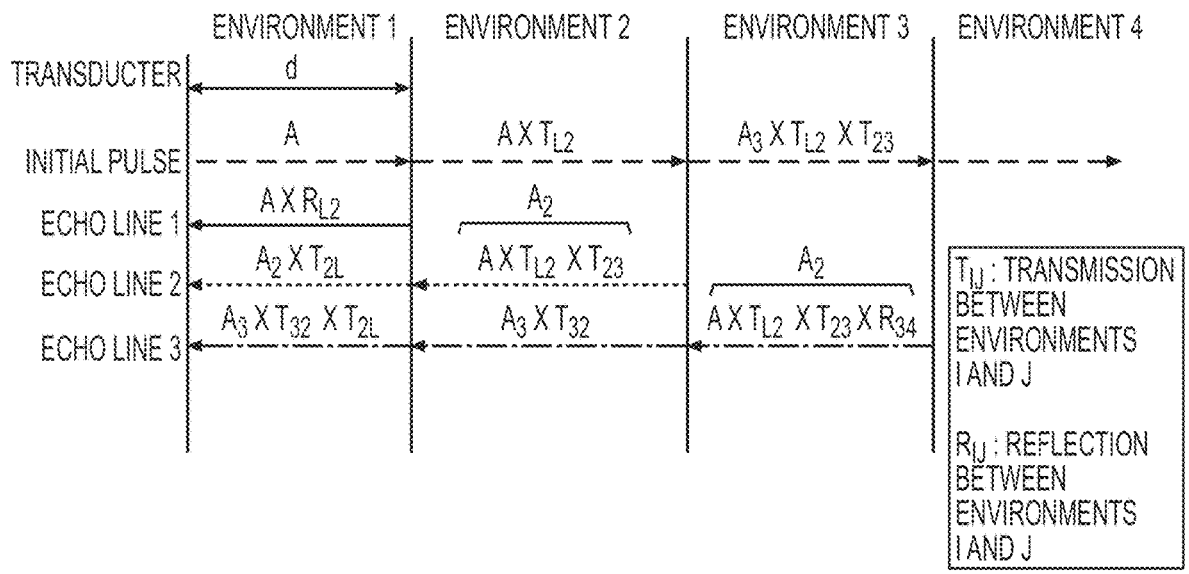

The present disclosure is drawn to systems and methods for non-invasive implant monitoring and rupture detection, among other aspects. In some embodiments, an electronic system may receive information corresponding to one or more images, e.g., ultrasound images, of a patient. The information may then be analyzed by the electronic system, e.g., using mathematical models that approximate implants in a normal state and implants having one or more defects. The analysis may include determining patterns based on a database of prior medical procedures and/or simulations. The electronic system may facilitate detection of abnormalities in an implant and/or placement thereof in a patient, to aid in the monitoring and detection of irregularities, such as implant ruptures.

While aspects of the present disclosure relate to breast implants, the discussion is not so limited and may be used for any implantable medical devices prone to rupture.

Breast implants may be implanted in a subglandular (anterior to the pectoralis major muscle) or subpectoral (posterior to the pectoralis major muscle) location. After placement of a breast implant within a patient's body, a thin fibrous capsule or scar tissue normally forms around the implant. In some cases, pronounced fibrous capsule formation may cause the implant to change shape, squeeze the implant, and may cause capsular contracture, a common complication from a breast implant surgery. When capsular contracture occurs, a breast implant may have radial folds which may cause tearing in the implant's outer shell.

In the case of breast implants, an intracapsular implant rupture refers to a rupture of the implant shell wherein the filler material (e.g., silicone gel or saline solution) leaks outside the implant shell and remains within the fibrous capsule. An uncollapsed implant rupture may be defined as a tear of the implant shell and is considered an intracapsular rupture. An extracapsular silicone implant rupture refers to rupture of both the implant shell and the fibrous capsule, such that the filler material leaks outside the fibrous capsule into surrounding patient tissue. In some cases, bodily fluids, such as blood, may leak into the implant when an intracapsular or extracapsular rupture occurs.

Ultrasound, also referred to as sonography, is a non-invasive medical imaging technique useful for observing the environment surrounding a medical implant to scan for abnormalities. Ultrasound can be used to capture internal images of the body, such as muscles, organs, blood vessels, and other tissue, in addition to implants. An ultrasound machine typically includes a transducer and a processor, such as a central processing unit of a computer, connected to a display, such as a monitor. To collect images, the transducer may be placed on a patient's skin and passed over an area of the body to be imaged, wherein sound waves are emitted from the transducer. See, e.g., FIGS. 13A-13B and discussion below. The frequency of the sound waves is typically above 20 kHz, e.g., frequencies ranging between 1 MHz and 10 MHz. The sound waves pass through the body and are at least partially reflected back to the transducer after they bounce off relatively more dense structures, such as bodily tissue or an implant. The processor measures the echo intensities and speed of the sound waves, and converts these measurements to electronic images. The grayscale of the image provides an indication of anatomy, wherein brighter areas correspond to features with greater density.

FIG. 1A shows an exemplary graph of amplitude versus time of a measured sound wave. As shown, the sound wave has an initial amplitude A that undergoes reflections and transmissions depending on the patient's anatomy. These reflection and transmission characteristics may be analyzed to calculate coefficients to describe characteristics of medical implants and abnormalities, such as a rupture. Ultrasound systems provide a convenient and cost-efficient way to obtain images of a patient, such as images of a patient's breast implant, particularly compared to MRI imaging.

Figure 2A:
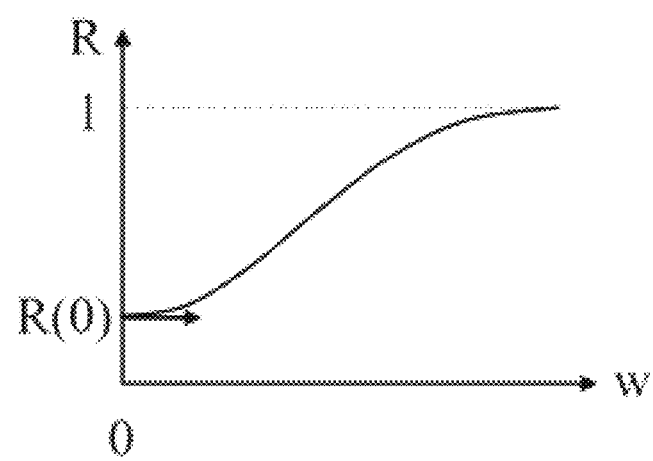
FIGS. 2A-2B illustrate reflection and transmission coefficients function of the frequency of the sound wave emitted by a transducer, according to some aspects of the present disclosure.
Figure 2B:
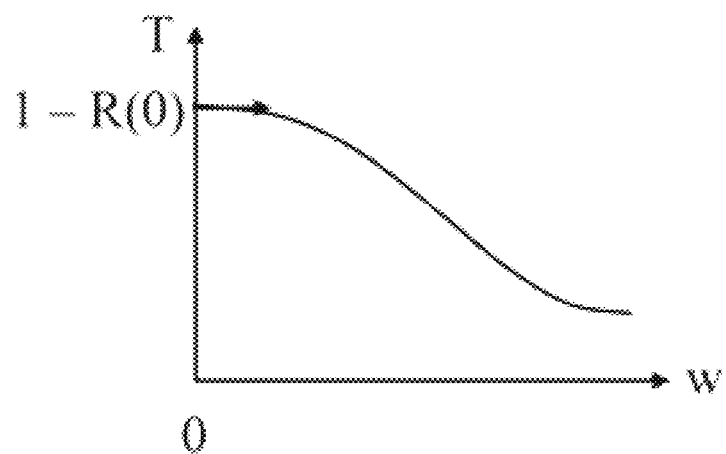

When a medical professional obtains images using an ultrasound system, a transducer sends a sound wave with an amplitude that changes due to reflection and transmissions as the sound wave contacts different types of anatomical structure. Reflection and transmission coefficients of the sound waves may be used to describe the environment around an implant and possible abnormalities in the implant, such as a rupture. FIGS. 2A and 2B show reflection and transmission coefficients (see Equations 1 and 2 below) function of the frequency of the sound wave (x-axis) emitted by a transducer. Reflection and transmission coefficients are a function of the frequency, and a function of compressibility and density.

$$R = \frac{(Z_1 - Z_2)^2 + \left[\frac{M_\omega}{S}\right]^2}{(Z_1 + Z_2)^2 + \left[\frac{M_\omega}{S}\right]^2} \qquad \text{Eq. 1}$$

$$T = \frac{4Z_1 Z_2}{(Z_1 + Z_2)^2 + \left[\frac{M_\omega}{S}\right]^2} \qquad \text{Eq. 2}$$

Further, $$N = \frac{D^2}{4\lambda} \text{ or } N = \frac{D^2 F}{4V}$$

where N=near field length or transition from near field to far field; D=diameter of the transducer; F=frequency of the transducer; $\lambda$=wavelength (cycles/second); and V=velocity of sound in the material. Low frequency may be used for high penetration of the tissue.

As in the equations above, in the below equation, $Z_1$ and $Z_2$ represent the acoustic impedance in two different media, wherein acoustic impedance is a function of compressibility and a property of the medium (material) in which the sound wave propagates.

$$\begin{cases} R(x) = \left[\dfrac{1-x}{1+x}\right]^2 \\ T(x) = \dfrac{4x}{(1+x)^2} \end{cases} \text{ with } x = \dfrac{Z_2}{Z_1} \qquad \text{Eq. 3}$$

if $Z_1 \approx Z_2$ there is almost total transmission

When the difference between $Z_1$ and $Z_2$ is large, a strong reflection will be shown in the ultrasound image. When there are inhomogeneities in the material being viewed with the ultrasound, there will be different impedances and therefore several reflections of the sound wave. For example, echo lines in an ultrasound image indicate inhomogeneities in a material. In the equation below, $Z_i$ is the acoustic impedance (Pa·m/s) of the environment i:

$$Z_i = \sqrt{\dfrac{\rho_i}{\chi_{s,i}}} = \rho_i * c_i \qquad \text{Eq. 4}$$

with 
$\begin{cases} \rho_i \text{: density of environment } i \\ \chi_{s,i} \text{: isothermal compressibility of environment } i \\ c_i \text{: speed of the sound in the environment } i \end{cases}$ The above equations provide insight into features of ultrasound images and possible causes of an irregularity.

An ultrasound image is produced based on the reflection of the sound waves off of a patient's anatomy, and allows for visualizing the contours of an implant within a patient. The strength (amplitude) of the sound signal and the time it takes for the wave to travel through the body provide information that may be used to produce an image. Ultrasound images are typically in grayscale, and in some examples may be in .bmp image format with a bit depth of 8 bits.

The present disclosure includes systems comprising algorithms that allow a user to input ultrasound images of a patient's implant and surrounding anatomy, and the system then may analyze the inputted images using mathematical models, artificial intelligence, databases of data related to the patient and/or the procedure, and/or the data the system has acquired using images from prior procedures. The systems herein may output a determination or conclusion, e.g., a probability, as to the presence of a rupture or other irregularity or abnormality in the implant.

In some examples, the system may assess the integrity of an implant shell, detect the positioning of an implant and whether or not it has moved, e.g., rotated or flipped, from a reference position (e.g., the initial or normal position following implantation), and/or detect periprosthetic breast capsules. In some examples, the system may use artificial intelligence to detect implant ruptures and/or other attributes of ultrasound images of implants. Different mathematical models may be incorporated into such a system to model particular features of an ultrasound image, such as the surface of an implant, and facilitate detection of various types of implant failures, such as ruptures. In some aspects, the systems and methods of the present disclosure may include mathematical models developed to model (simulate) one or more features, such as implant folds, seromas, capsule ruptures, true granulomas. Additionally or alternatively, the systems and methods herein may employ embedded markers used to verify the position or alignment of an implant, and/or other aspects of a medical implant.

Below are descriptions of mathematical models that provide a means for describing various features of an implant shown in an ultrasound image and/or for use in generating sample ultrasound images of medical implants.

One example of a mathematical model that may be incorporated into a system of the present disclosure uses a sine function that changes the intensity of pixels, e.g., according to a greyscale range, in an image vertically to describe the surface of an implant. For example, below is an exemplary sine function for describing the surface of an implant in an ultrasound image.

$$I(i, j) = A * \sin\left(\dfrac{2*pi*i}{T}\right) \text{ with} \qquad \text{Eq. 5}$$

$\begin{cases} I(i,j) \text{: intensity of the pixel line } i \text{ column } j \\ T \text{: the spatial period in pixel vertically} \end{cases}$ The mathematical model shown above may be used to model (simulate) the surface of a medical implant without any irregularities (e.g., an exemplary implant free from ruptures and other surface defects). This model may take into account the type of implant and typical surfaces of the implant, e.g., such that the results are dependent on the particular type of medical implant.

Figure 3:
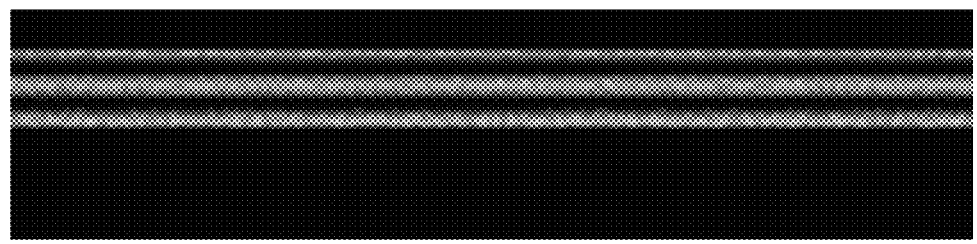
FIG. 3 shows an ultrasound image of an implant surface, according to some aspects of the present disclosure.

In the above-described sine function describing the surface of an implant, the number of oscillations, and the period of the sine function may be used to describe the implant surface. For example, FIG. 3 depicts an ultrasound image of a surface of a breast implant, showing three separated lines. The three lines represent (1) the interface between the muscle (or fat) and the fibrous tissue around the implant shell, (2) the interface between the fibrous tissue and the implant shell, and (3) the interface between the implant shell and the implant filling material. The disposition of the three lines shown in FIG. 3 may allow for identification of the type of implant. In some examples, the thickness of the line between the first two echogenic lines, as shown in FIG. 3, may provide information about the thickness of the fibrous tissue of the patient adjacent to the implant. The surface shown in FIG. 3 may be modeled using a sine function, such as the function discussed above. In some examples, the spatial period, which is the distance that separates two consecutive echogenic lines, may provide information on the configuration and materials used for the implant surface, such as the layers of a breast implant shell. Properties of the shell, such as the number of layers, configuration of layers, the material(s) used in each layer, may affect the acoustic impedance, and reflection and transmission coefficients. In some examples, the spatial period may range from about 5 pixels to about 15 pixels, e.g., about 10 pixels, however the spatial period may be any other range of pixels, e.g., based on the types and arrangement of materials of the implant. The lines may be equidistant, or the spacing between lines may vary.

A granuloma is an indicator in an ultrasound image of a rupture in a breast implant. Another example of a mathematical model that may be incorporated into the systems herein is a gauss function that may be used to describe granulomas in an ultrasound image. The below equation is a gauss function, in two dimensions, that depends on the vertical and horizontal pixels x and y of an ultrasound image.

$$f(i, j) = A * \exp\left(-\left(\frac{(i-i_0)^2}{2*\sigma_i^2} + \frac{(j-j_0)^2}{2*\sigma_j^2}\right)\right) \quad \text{Eq. 6}$$

Figure 4:
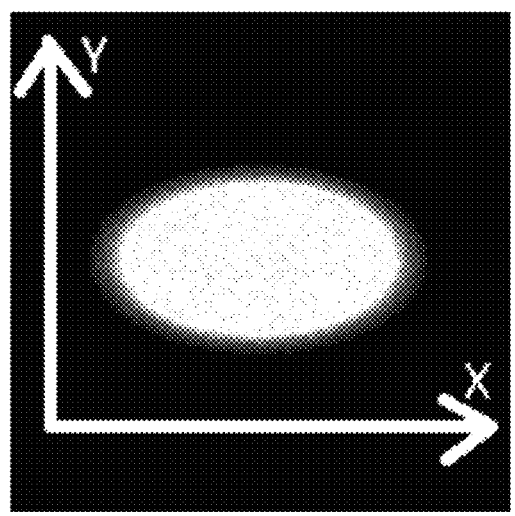
FIG. 4 illustrates a granuloma, according to some aspects of the present disclosure.

FIG. 4 shows an exemplary granuloma with x and y coordinate axis. The gauss function described above may provide a mathematical model for such a granuloma shown in FIG. 4. By utilizing the gauss function shown above, sample ultrasound images may be created to simulate a granuloma in order to mimic another type of irregularity in an implant. These sample images may be used by the systems and methods disclosed herein to train an artificial intelligence system to detect granulomas in ultrasound images. The above gauss function may also be used to categorize granulomas, for example by using the parameters of the function and/or comparing distances between features of the sample images created using the gauss function with real ultrasound images of implants.

Figure 5:
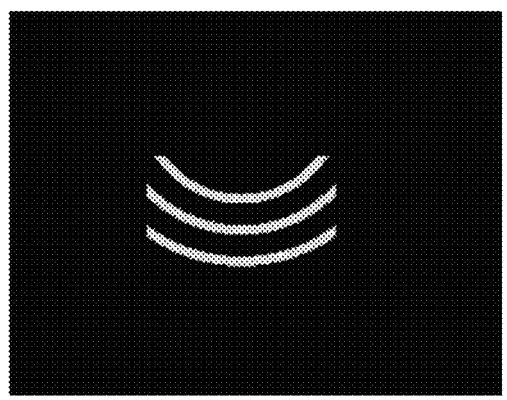
FIG. 5 illustrates echo lines, according to some aspects of the present disclosure.

Echo lines, such as the lines shown in FIG. 5, may appear in ultrasound images of breast implants. Echo lines in an ultrasound image are a sign of inhomogeneities in an environment. The systems herein may model echo lines by describing them using the radius of each curved line and distance between the lines. Echo lines on a surface of the implant may be indicative of a rupture.

Figure 6:
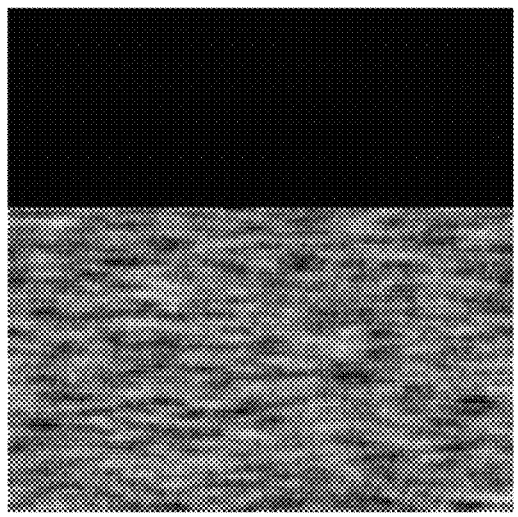
FIG. 6 illustrates a snowstorm feature, according to some aspects of the present disclosure.

FIG. 6 shows an exemplary snowstorm feature that may be identified in an ultrasound image of an implant. In an ultrasound image of a breast implant, a snowstorm feature may be an indicator of an extracapsular rupture. For example, a snowstorm feature may indicate the presence of free silicone droplets (e.g., of an implant with a silicone gel filling) mixed with breast tissue, e.g., giving a characteristic heterogeneous echogenic appearance with the dispersion of the ultrasound beam. A snowstorm may be mathematically modeled by making a convolution of a black image with a Gaussian function, then a convolution of the result with a rectangular function in two dimensions. A snowstorm may be described by the length of the rectangular function and the parameter of the gauss function.

Figure 7:
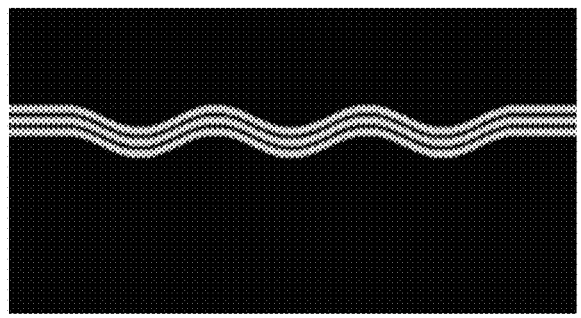
FIG. 7 illustrates an ultrasound image of an implant surface with a sinusoidal curve indicative of an implant contracture, according to some aspects of the present disclosure.

Implant contractures may be mathematically described in the systems herein with a sine function in intensity of the pixels (vertically) and a sine function that makes the surface of an implant in the ultrasound image change amplitude. For example, FIG. 7 shows an exemplary ultrasound image of an implant surface with a sinusoidal curved surface, which may correspond to sinusoidal variations of the implant surface. In some cases, the curved surface may be indicative of an implant contracture, e.g., in addition to sinusoidal variations of the implant surface itself. Below are exemplary functions for describing a contracture in an ultrasound image. Note in the below exemplary contracture model, the contractures may be described by the amplitude B of the variation.

$$I(i, j) = A * \sin\left(\frac{2*pi*i}{T_1}\right) \text{ with} \quad \text{Eq. 7}$$

$\begin{cases} I(i, j)\text{: intensity of the pixel line } i \text{ column } j \\ T_1\text{: the spatial period in pixel vertically} \\ A\text{: the amplitude of the sinus function} \end{cases}$ $$i = \text{floor}\left[B * \sin\left(\frac{2*pi*j}{T_2}\right)\right] \text{ with} \quad \text{Eq. 8}$$

$\begin{cases} T_2\text{: the spatial period in pixel of the variation of the surface} \\ B\text{: the amplitude of the sinus function} \end{cases}$ Sample ultrasound images may be created to simulate a contracture as another irregularity of an implant. For example, the above exemplary contracture model may assist with creating sample ultrasound images showing implant surface irregularities. These sample images may be used by the systems and methods disclosed herein to train an artificial intelligence system to detect contractures in ultrasound images. The above contracture mathematical model may also be used to categorize contractures, for example by using the parameters of the function and/or comparing distances between features of the sample images created using the contracture model with real ultrasound images of implants.

By utilizing one or more of the above-described mathematical models to describe features in an ultrasound image, systems according to the present disclosure may identify certain features in an ultrasound image of an implant, such as a breast implant. For example, an implant may be described and can be differentiated from the surrounding tissues using the period of the sinusoidal variation of the intensity of the pixels vertically and the number of visible lines shown in the ultrasound image. Any of the mathematical models described herein and combinations thereof may be used to create sample ultrasound images useful for training an artificial intelligence system. For example, the mathematical models described herein may be used to populate a database of sample ultrasound images of various types of medical implant irregularities, such as ruptures and contractures, for analysis of real ultrasound images. In some aspects of the present disclosure, a single sample ultrasound image may be created using a plurality of the mathematical models described herein, wherein the image may include a plurality of different implant irregularities and/or different types of implant irregularities. Exemplary systems herein may include a combination of at least two of the above mathematical models. The database may also include real ultrasound images and corresponding labels as to the presence or absence of an abnormalities, such as a rupture, contracture, or other defect. In some examples, the database includes all real ultrasound images, each image associated with a label identifying the presence or absence of one or more types of implant defects.

In some examples, the systems disclosed herein may include a processor programmed with algorithms to analyze ultrasound images, transform the data into mathematical models to recognize certain features, and then derive an indication of the probability that one or more implant failures are present in the image. For example, the system may output an indication of the probability (e.g., from 0 to 100%, or from 0.1% to 99.9%, etc.) that an image includes an implant rupture. In some examples, the system may output a vector of numbers ranging between 0 and 1 indicative of the probability of a phenomenon, such as a type of defect (e.g., rupture, contracture, etc.) or the absence of a defect. Some examples of the disclosed system may process the vector of numbers by comparing the maximum value of the vector with a fixed value, such as 0.5. If the vector's maximum value is lower than 0.5, the system may classify the object in an "unknown" category, and if the vector's maximum value is equal to or greater than 0.5, the object (e.g., identified feature on an ultrasound image) may be classified in a category of objects the system associates with the particular vector.

In order to provide the system with a database to use for analyzing images without real images from patients, simulated ultrasound images of medical implants may be used to create a database for a system. A database of images may be obtained from patient data (ultrasound images corresponding to imaging of a patient with or without implant ruptures or other abnormalities) and/or from simulated images. Simulated images may include images taken of implants outside the body with or without features intended to simulate ruptures or other abnormalities that may occur inside a patient (e.g., cuts made in the surface of the implant). Additionally or alternatively, simulated images may include images that are constructed electronically with features indicative of implants and possible ruptures.

In some examples, simulated images may include images generated using one or more of the mathematical models described herein. In some examples, a database may include a combination of simulated images and real ultrasound images from prior medical examinations. The database may include at least 5,000 images, e.g., at least 20,000 images, at least 50,000, at least 75,000 images, or 100,000 images or more. For example, the database may include from 10,000 to 50,000 images; from 10,000 to 100,000 images; from 50,000 images to 75,000 images; or any other number of images. The use of simulated/sample ultrasound images according to the methods herein is useful for populating a database with a sufficiently large number of images representing different implant irregularities. In some examples, a medical professional may assist with populating a database by identifying features present in sample ultrasound images, such as a granuloma or a rupture, generated according to the methods herein and associate a corresponding label for each image. The image and corresponding label may be stored in the database for the system (e.g., artificial neural network) to use during analysis of ultrasound images of a patient to assist in identifying possible implant defects or other complications associated with an implant.

Figure 8A:
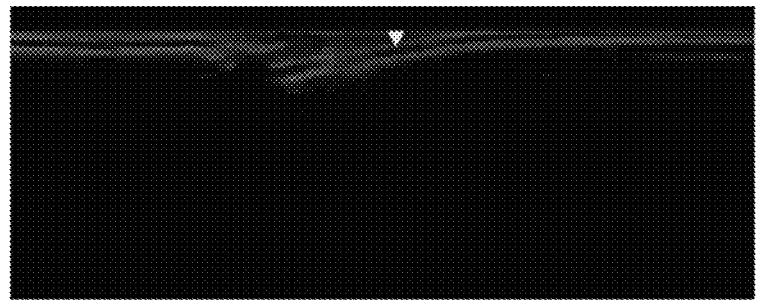
FIGS. 8A-8B show ultrasound images of implant surfaces with simulated ruptures, according to some aspects of the present disclosure.
Figure 8B:
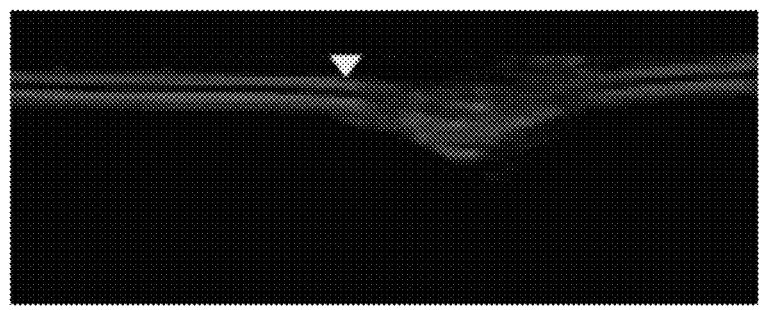

FIGS. 8A and 8B show examples of ultrasound images of surfaces of a breast implant that include simulated surface failures. The images correspond to two different types of ruptures simulated by cutting the surfaces of silicone gel-filled breast implants. FIG. 8A shows an example of a breast implant filler leak, such as a silicone leak, caused by a discontinuity in the surface of the implant. The filler material leaking outside the implant shell appears as the surface discontinuity. FIG. 8B shows an example of an implant surface with a rupture, wherein the filler material remains inside the implant. This type of rupture does not show a discontinuity in the surface of the implant as in FIG. 8A. Rather, the rupture in FIG. 8B appears as an inhomogeneity on the implant surface due to a scattering of the ultrasound pulse.

When a rupture is present in an ultrasound image of an implant, an abnormal zone of the surface of the implant may be shown in the ultrasound image compared to the normal zone of the surface. In some examples of the present disclosure, the system may detect the normal zone and the abnormal zone of the surface of an implant in an ultrasound image. In some examples, the system may recognize an abnormal zone by comparing the zones of the implant to a normal zone of the implant based on images taken of normal versions of that type of implant.

Figure 9:
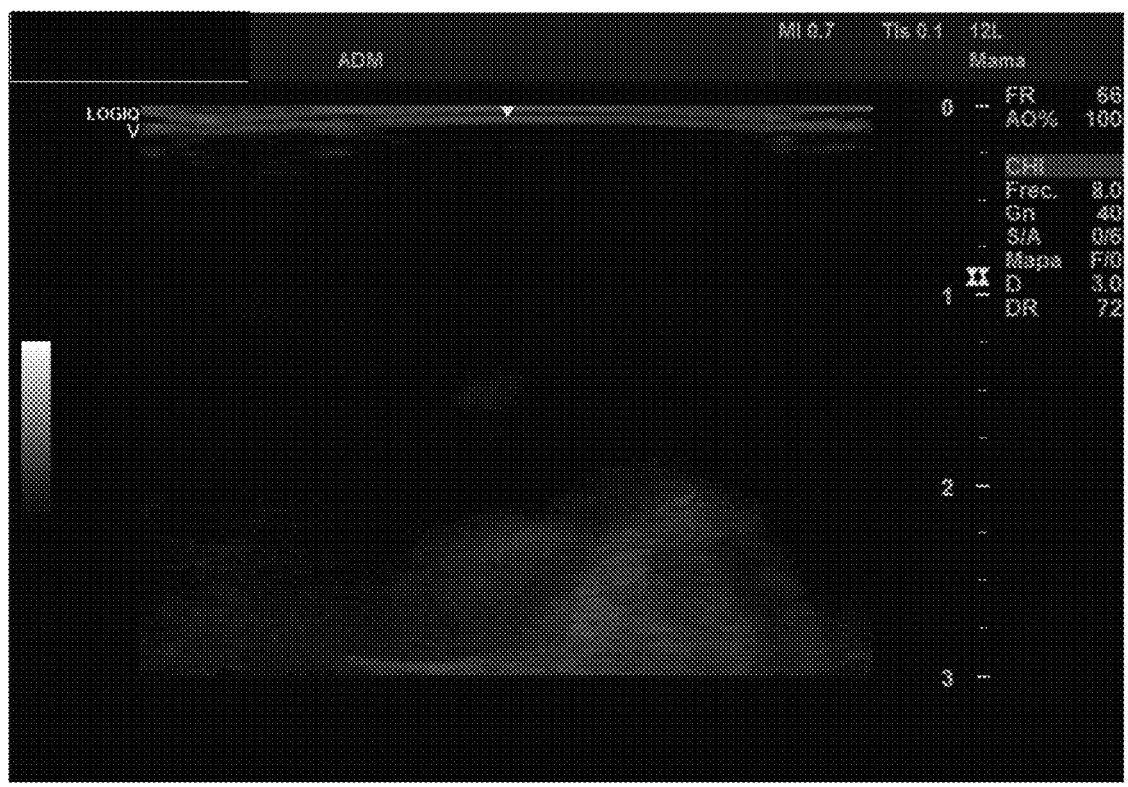
FIGS. 9-11 show additional ultrasound images of implants, according to some aspects of the present disclosure.

FIG. 9 illustrates a simulated ultrasound image of a snowstorm. The image in FIG. 9 was created by injecting inside a breast implant water at 20° C., which has almost the same density as blood at 37.5° C. Since a snowstorm is a sign of extracapsular rupture in a breast implant, blood may leak into the implant and could create inhomogeneities inside the implant. Accordingly, injecting the water at 20° C. simulates blood leaking into the implant.

Figure 10:
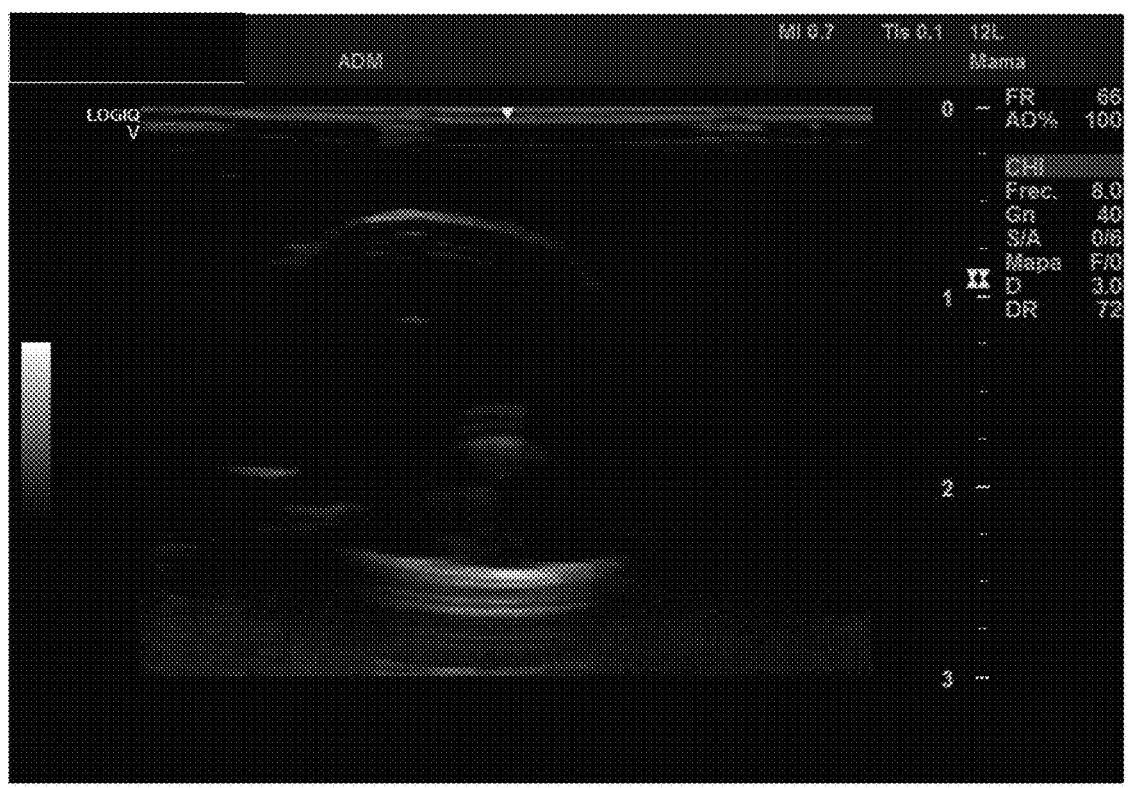
Figure 11:
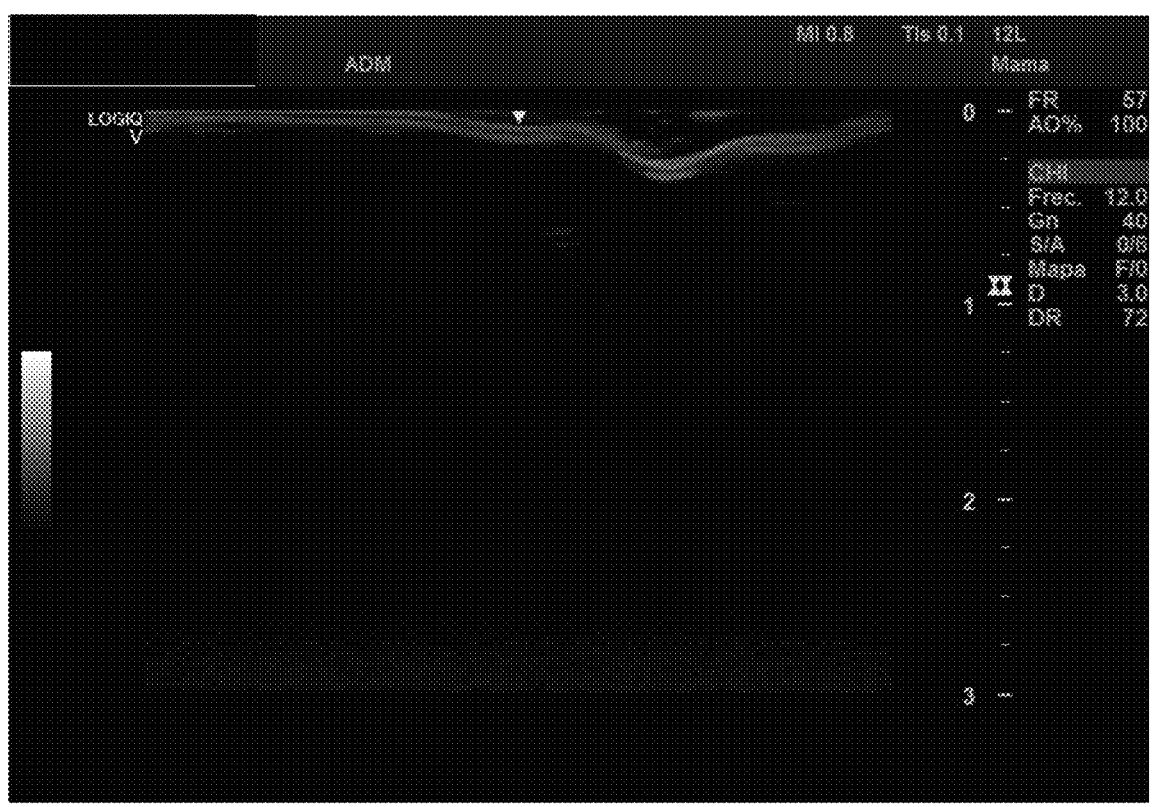

FIG. 10 illustrates another example of a simulated ultrasound image of an implant. In FIG. 10, echo lines were simulated by injecting air into a breast implant, which caused reverberations in the implant due to the difference of acoustic impedance. As a result, the ultrasound image of the breast implant shows echo lines caused from the injected air. FIG. 11 illustrates yet another example of a simulated ultrasound image of an implant. FIG. 11 shows a contracture which was simulated by taking an ultrasound image of a breast implant with thread applying pressure over the surface of the implant. The thread applying pressure over the surface of the implant mimics the pressure applied by muscle fibers to an implant in a patient's body, causing contractures. Any or all of the images shown in FIGS. 9, 10, and 11 may be used to build a database of simulated images. A database of simulated images may be used by a system to calculate and analyze inputted real ultrasound images in order to detect implant irregularities.

Figure 12:
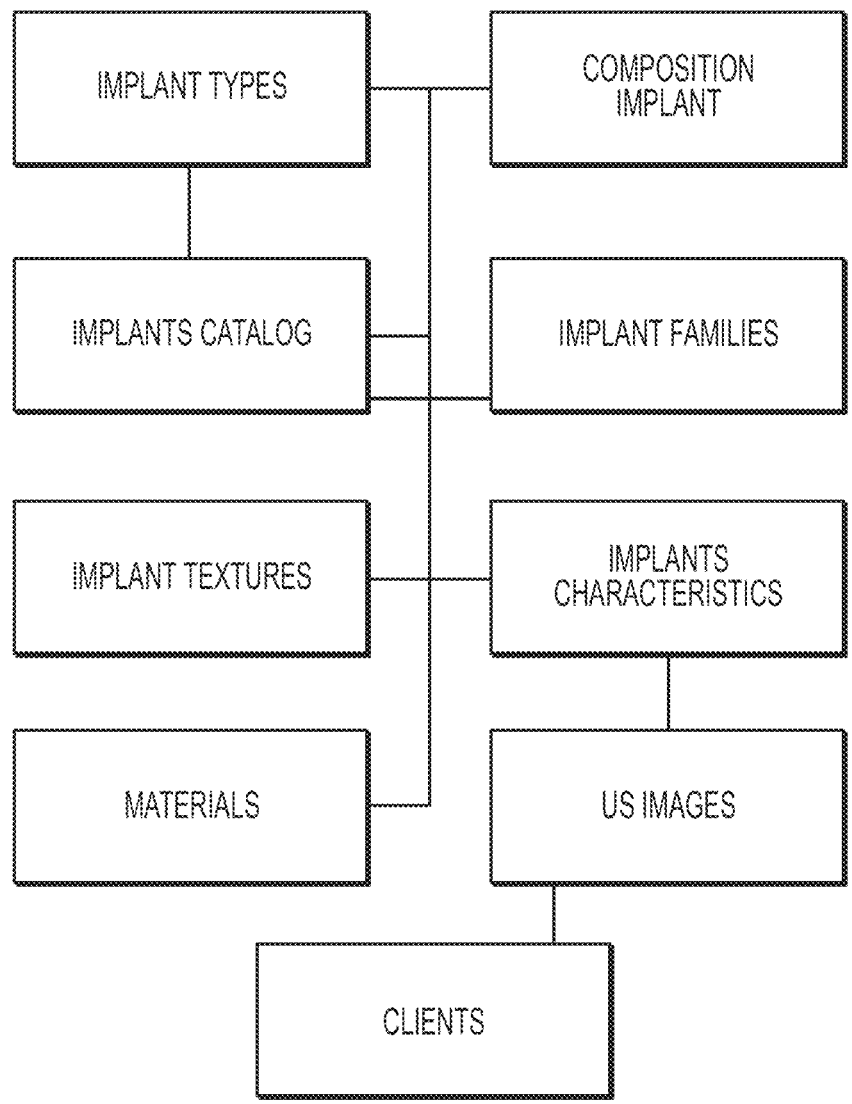
FIG. 12 illustrates a diagram of electronic databases, according to some aspects of the present disclosure.

The database of ultrasound images and/or other data from prior procedures may be utilized by the system (e.g., by the processor) to identify and classify features of an ultrasound image. For example, FIG. 12 illustrates various types of data (implant types, implants catalog, implant textures, materials, composition of implant, implant families, implant characteristics, images, and client data) that may be stored in databases and used by a system to detect characteristics of a medical implant using an ultrasound image.

As mentioned above, the systems herein may include a processor, wherein the processor may be utilized to implement the various functions (e.g., calculations, processes, analyses) described herein. The systems herein may be separate from an ultrasound imaging device. For example, the system may be configured to receive images previously obtained from an ultrasound imaging device, e.g., images stored in a database as discussed above. In some examples, the systems and processor functions herein may be incorporated into an ultrasound imaging device, e.g., such that a processor may perform the functions described herein and/or other functions associated with the ultrasound imaging device.

The systems herein may include a processing circuit that also includes memory. The processor can be implemented as a general purpose processor, an application specific integrated circuit (ASIC), one or more field programmable gate arrays (FPGAs), a group of processing components, or other suitable electronic processing components. Memory (e.g., memory, memory unit, storage device, etc.) may be one or more devices (e.g., RAM, ROM, Flash-memory, hard disk storage, etc.) for storing data and/or computer code for completing or facilitating the various processes described in the present application. Memory may be or include volatile memory or non-volatile memory. Memory may include database components, object code components, script components, or any other type of information structure for supporting the various activities described in the present application. According to an exemplary embodiment, memory may be communicably connected to a processor and may include computer code for executing one or more processes described herein. The memory may contain a variety of modules, each capable of storing data and/or computer code related to specific types of functions. In one embodiment, memory contains several modules related to medical procedures, such as an input module, an analysis module, and an output module.

It should be understood that the system processor need not be contained in a single housing. Rather, components of the system processor may be located in various locations, or even in a remote location. Components of system processor, including components of a processor and memory, may be located, for example, in components of a remote network server, a computer, a portable electronic device, a network of computers, among other examples.

The present disclosure contemplates methods, systems, and program products on any machine-readable media for accomplishing various operations. Any of the systems described herein may include a machine-readable media. The machine-readable media may be part of or may interface with the system processor. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Figure 14A:
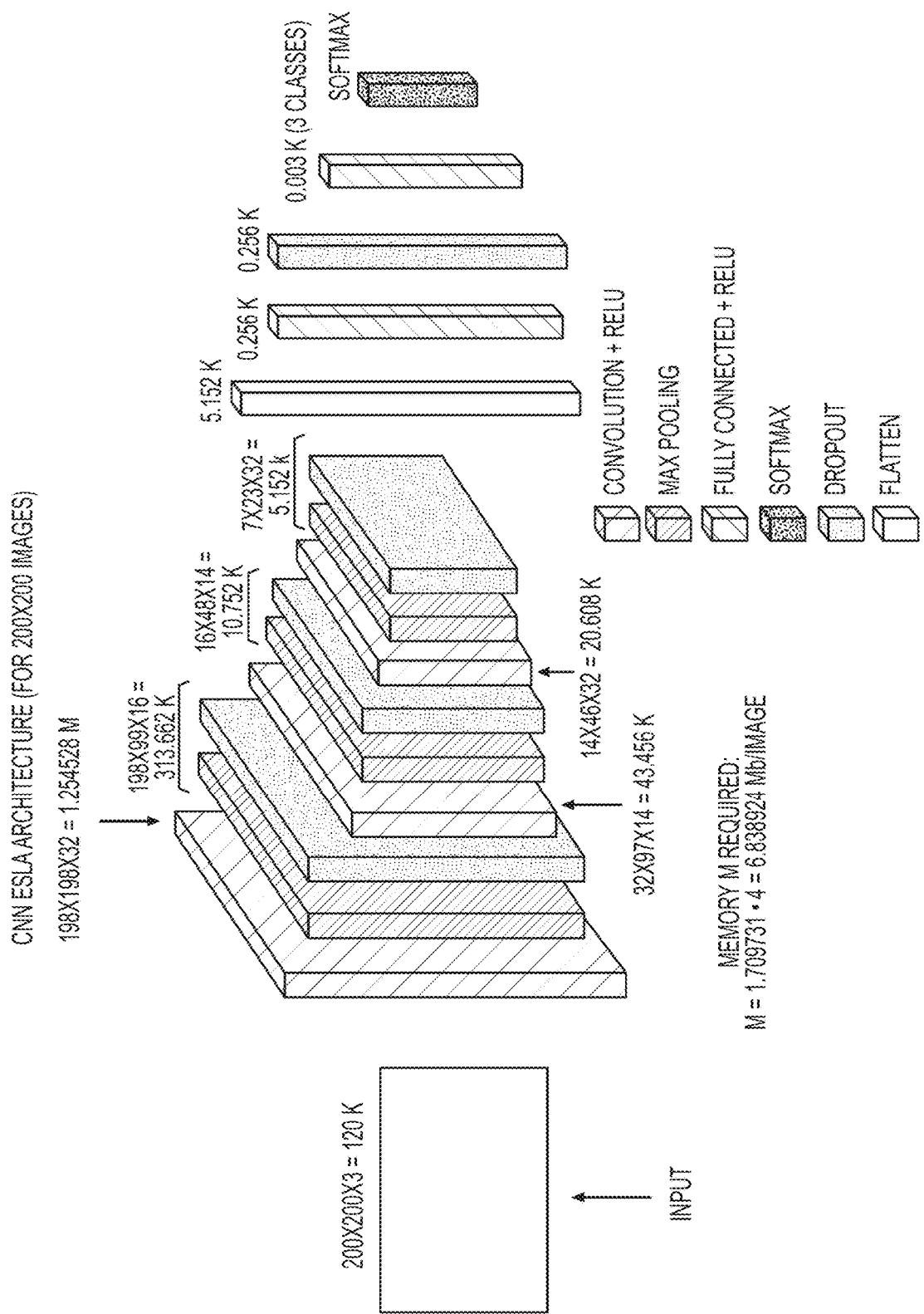

The systems herein may employ artificial intelligence during analysis of images to determine whether the images are indicative of an implant rupture or other irregularity or abnormality. For example, the processor of the system may include software based on artificial neural networks, which typically include neurons or processing elements and connections that are organized in layers. These layers may be structured hierarchically, with an input layer, an output layer, and middle or hidden layers. FIGS. 14A and 14B illustrate an example of a layered CNN ESLA Architecture for processing ultrasound images. Connection weights are "learned" by the network through inputting examples, such as example ultrasound images, from a training set of images into the network. The artificial neural networks may include any of the mathematical models discussed herein. In some examples, the architecture may include different layers and different types of layers. FIGS. 14A and 14B illustrate an example comprising three max pooling layers, three dropout layers, one flatten layer, two fully connected layers with Relu (rectified linear unit) activation functions, and one Softmax classifier. The input for the architecture may be an image, and the output may be a vector of numbers between 0 and 1. In some examples, the size of the vector of the output may be the number of categories of features the system may identify in the image, such as ruptures or contractures. In some aspects, each component of the output vector may be interpreted by the system as the probability that the input is within the respective category of features. Other examples of artificial intelligence architecture that may be used herein are shown in FIGS. 22A, 22B, 29A, and 29B. Results from training various artificial intelligence systems of the present disclosure are shown in the data in FIGS. 21A-21B, 23A-23B, 24A-24B, 25A-25B, 26A-26B, 27A-27B, 28A-28B, and 30A-30B.

Artificial intelligence may be incorporated into a processor of the present disclosure to compare ultrasound images, for example images stored in the processor, to images inputted into the system for analysis. In some examples, the system may utilize artificial intelligence when processing ultrasound images when comparing the ultrasound images to images from a database of ultrasound images. For example, the system may search different distances that could describe the difference between two images, such as distances between similar features in the inputted ultrasound images and the stored ultrasound images from one or more databases of the system. In some examples, the system may search the parameters of different mathematical models characterizing an image to reduce the distance between the mathematical model of a feature and the actual feature in the image. By comparing distances between mathematically modeled image features and the actual image features, the system may characterize specific features of the ultrasound images. For example, the system may distinguish between different types of a snowstorm feature in an image, such as a noise snowstorm and a regular snowstorm.

Figure 18A:
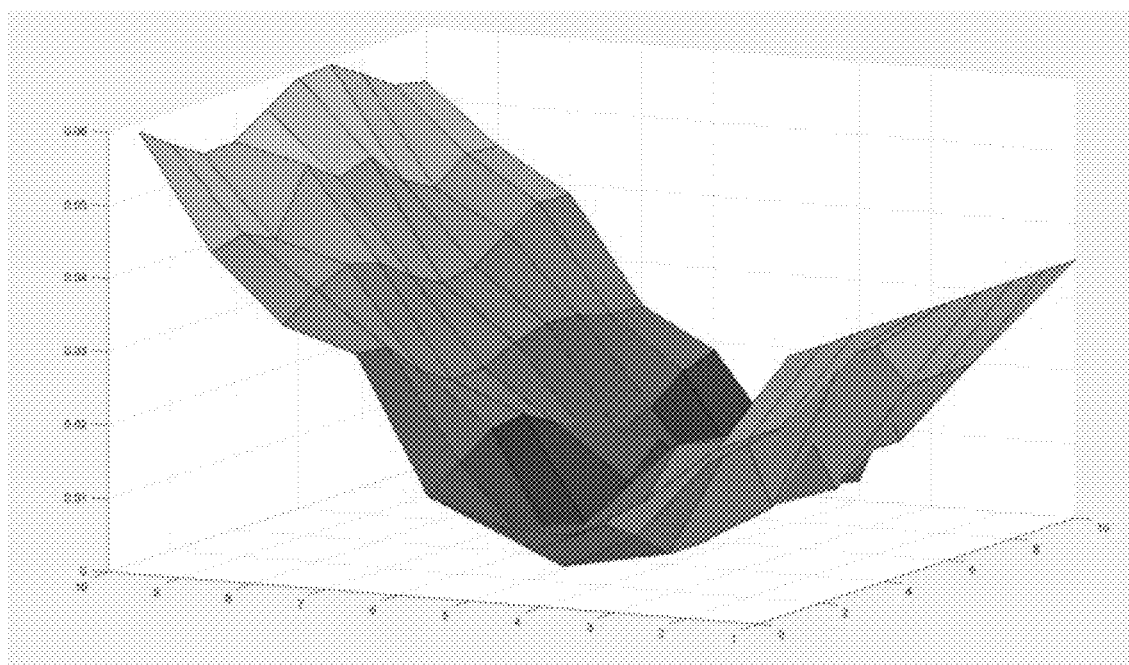
FIGS. 18A-18B illustrate three-dimensional graphs of variation of distance (vertical axis) between a real ultrasound image and a mathematical simulation with different parameters (horizontal axes) of a mathematical model for the surface of an implant, according to some aspects of the present disclosure.
Figure 18B:
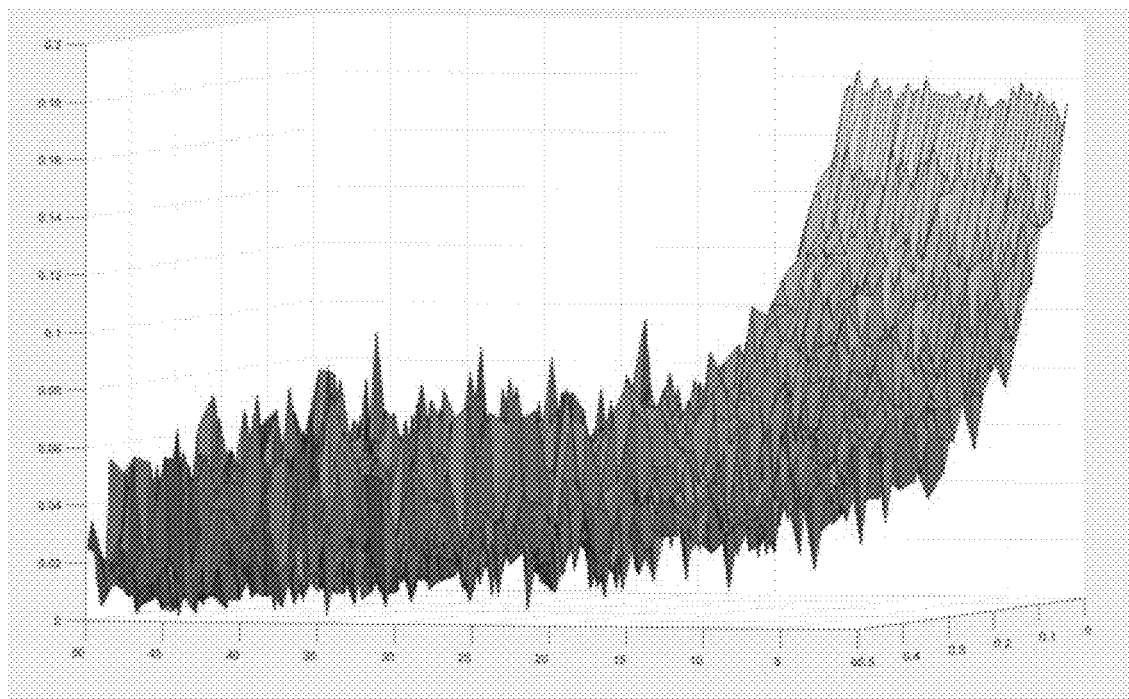
Figure 21A:
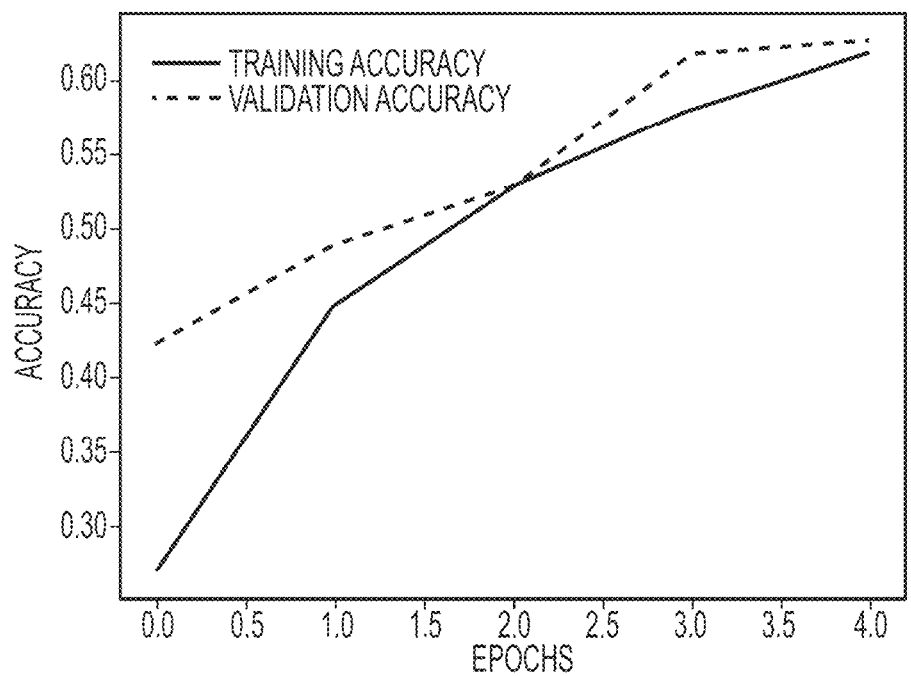
Figure 21B:
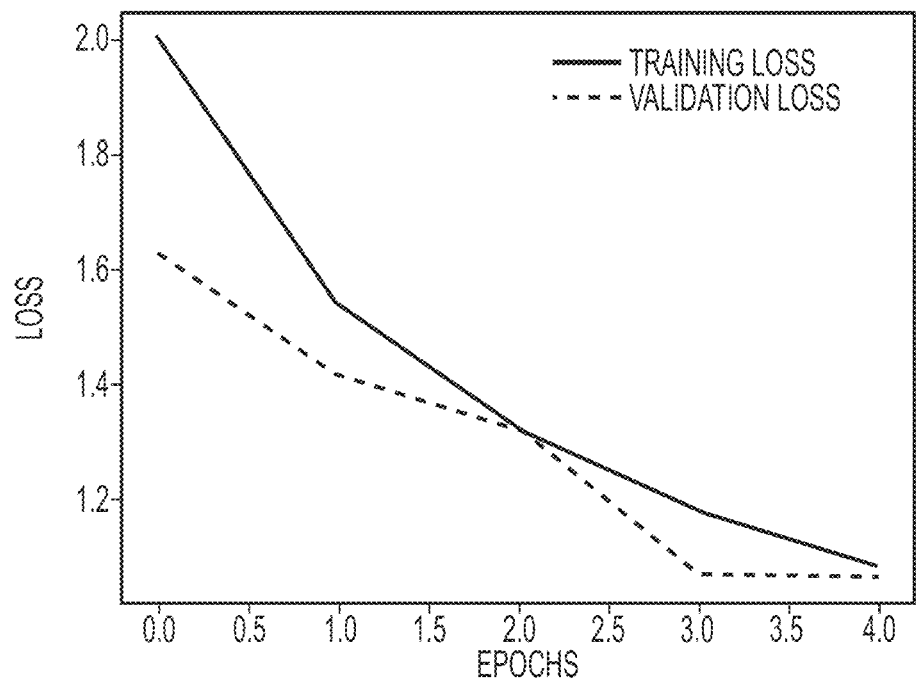
Figure 22A:
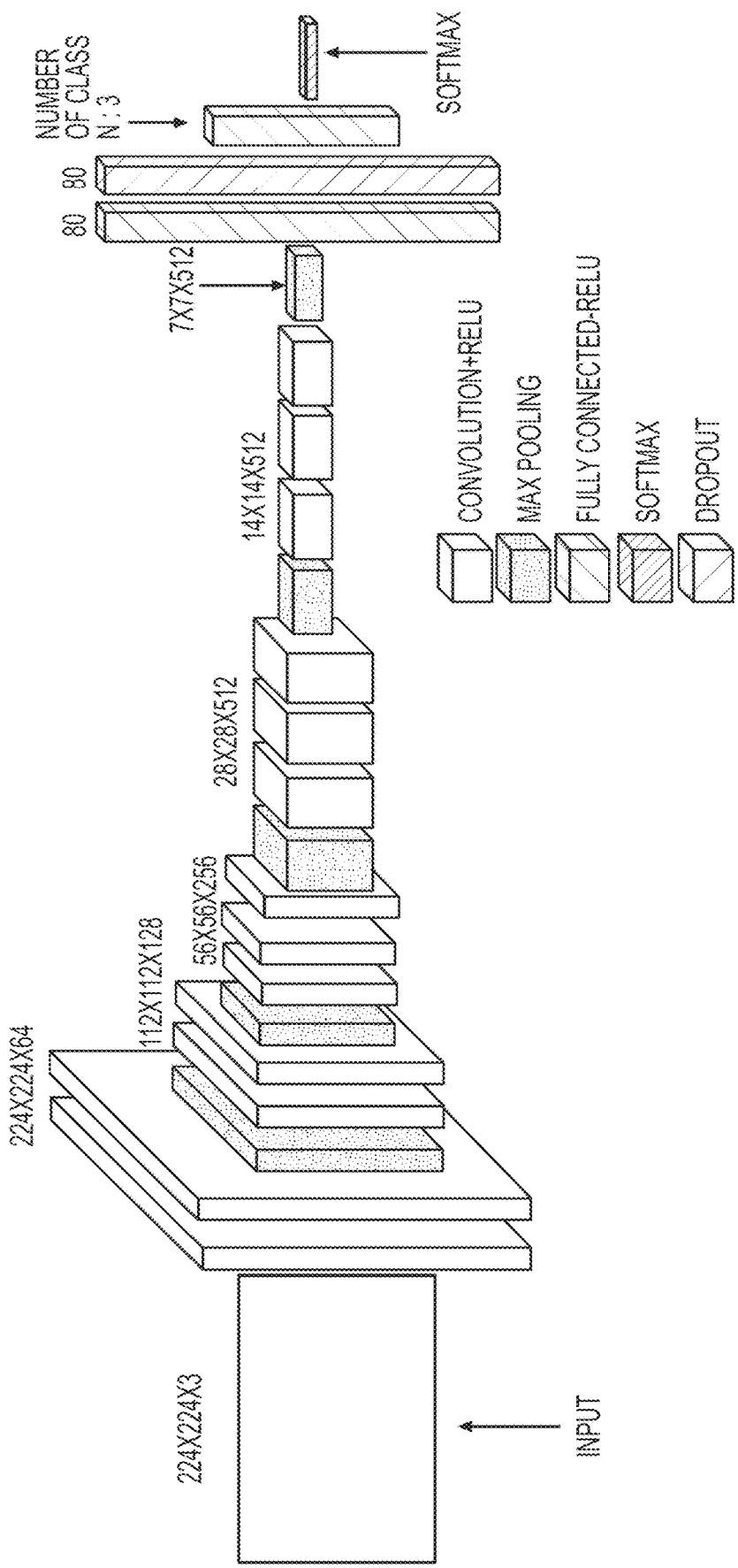
Figure 23A:
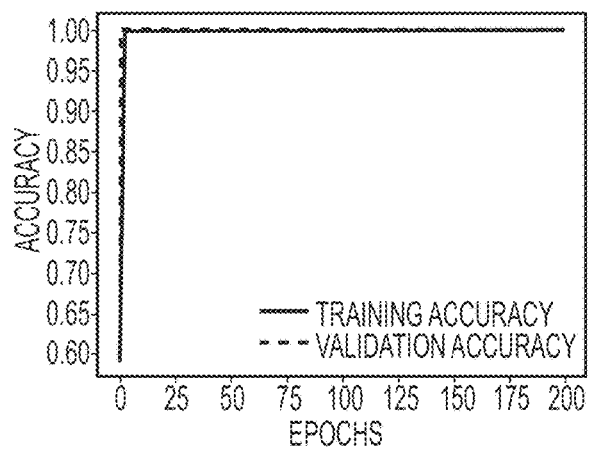
FIGS. 23A-23B, 24A-24B, 25A-25B, 26A-26B, 27A-27B, and 28A-28B illustrate training accuracy, validation accuracy, training loss, and validation loss curves for an artificial intelligence system, according to some aspects of the present disclosure.
Figure 23B:
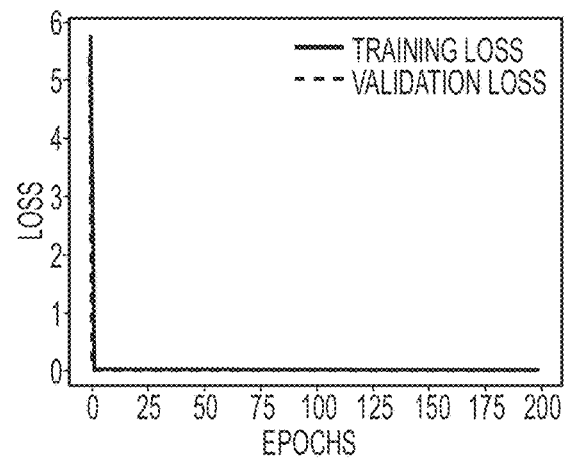
Figure 24A:
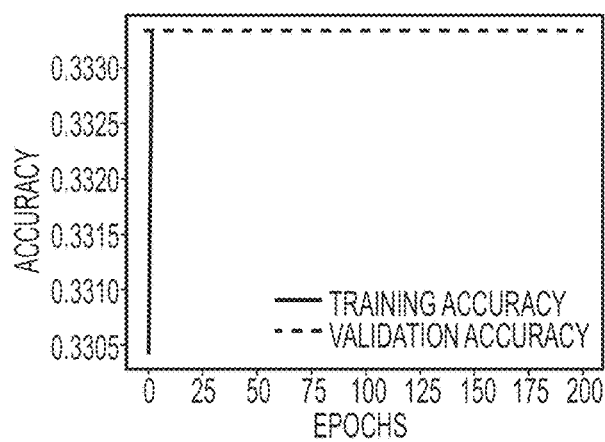
Figure 24B:
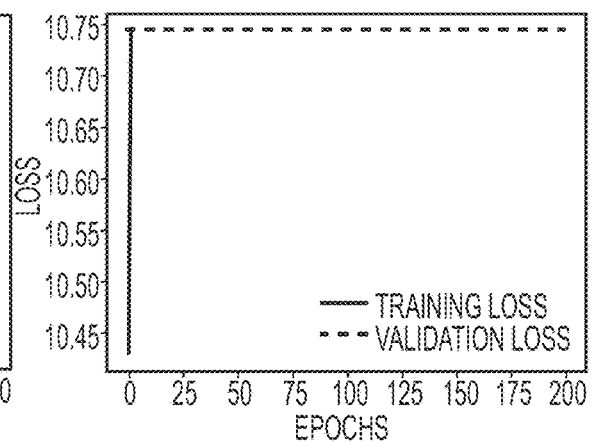
Figure 25A:
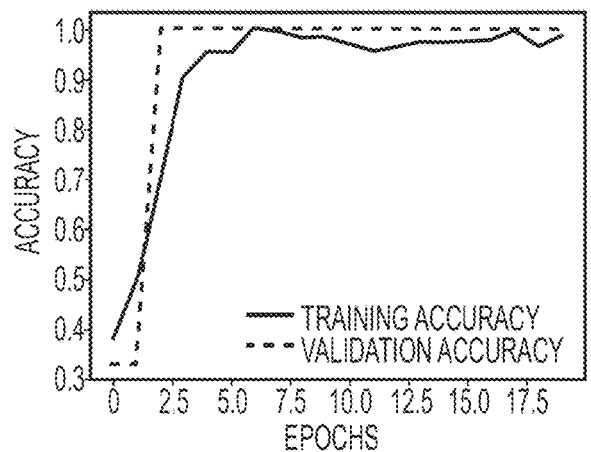
Figure 25B:
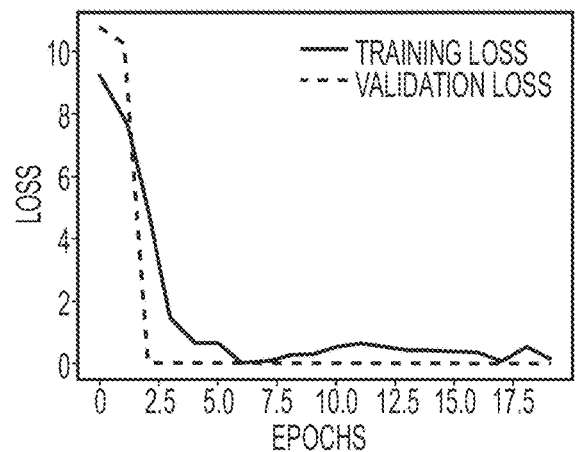
Figure 26A:
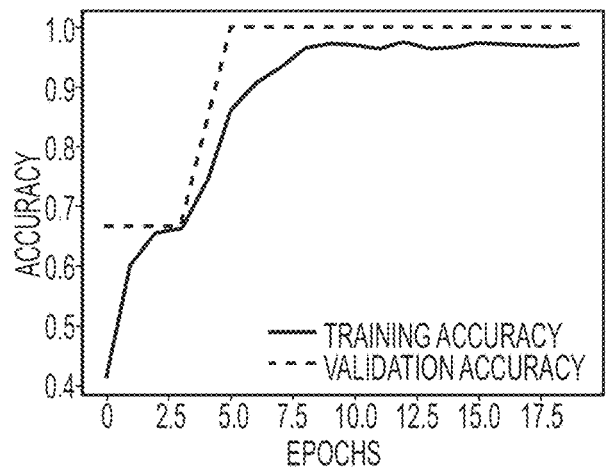
Figure 26B:
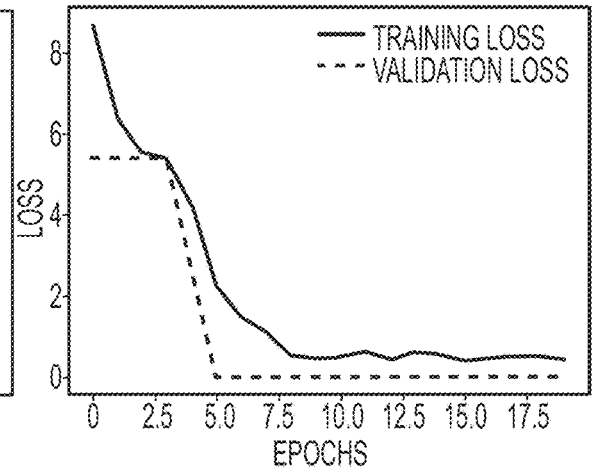
Figure 27A:
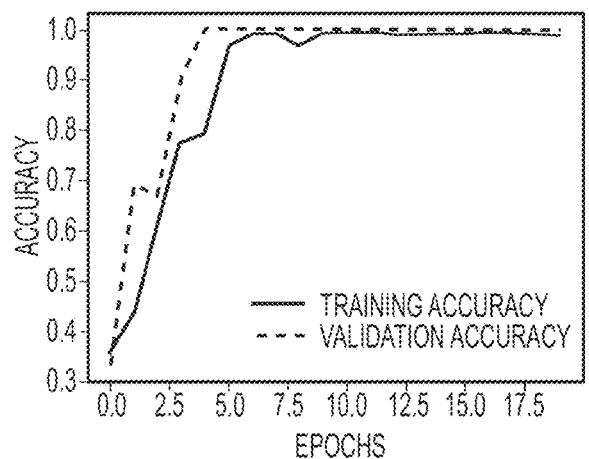
Figure 27B:
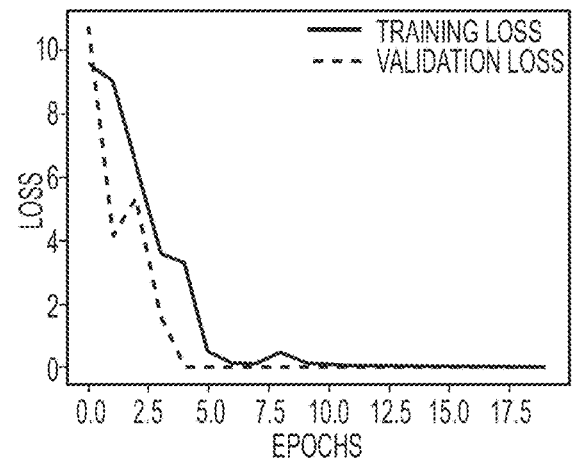
Figure 28A:
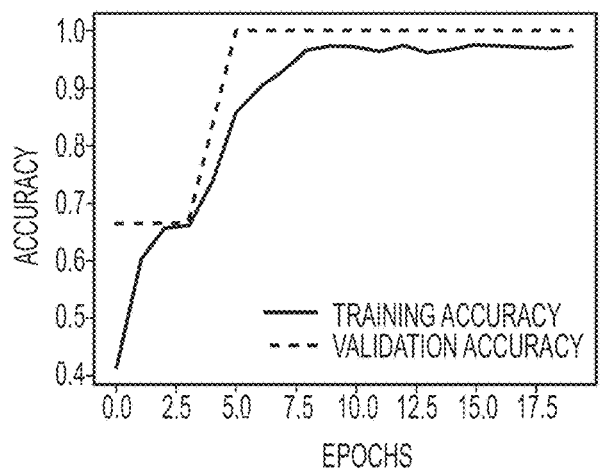
Figure 28B:
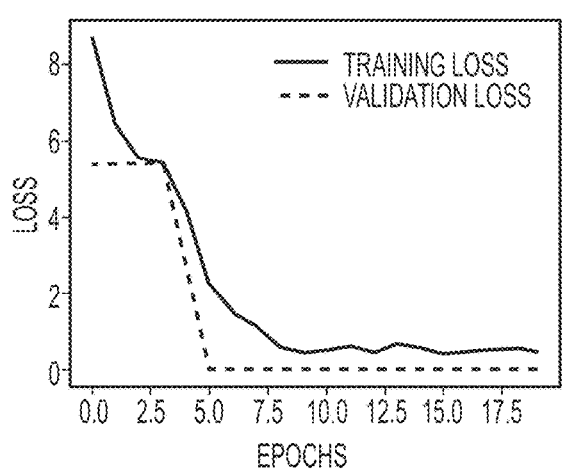
Figure 29A:
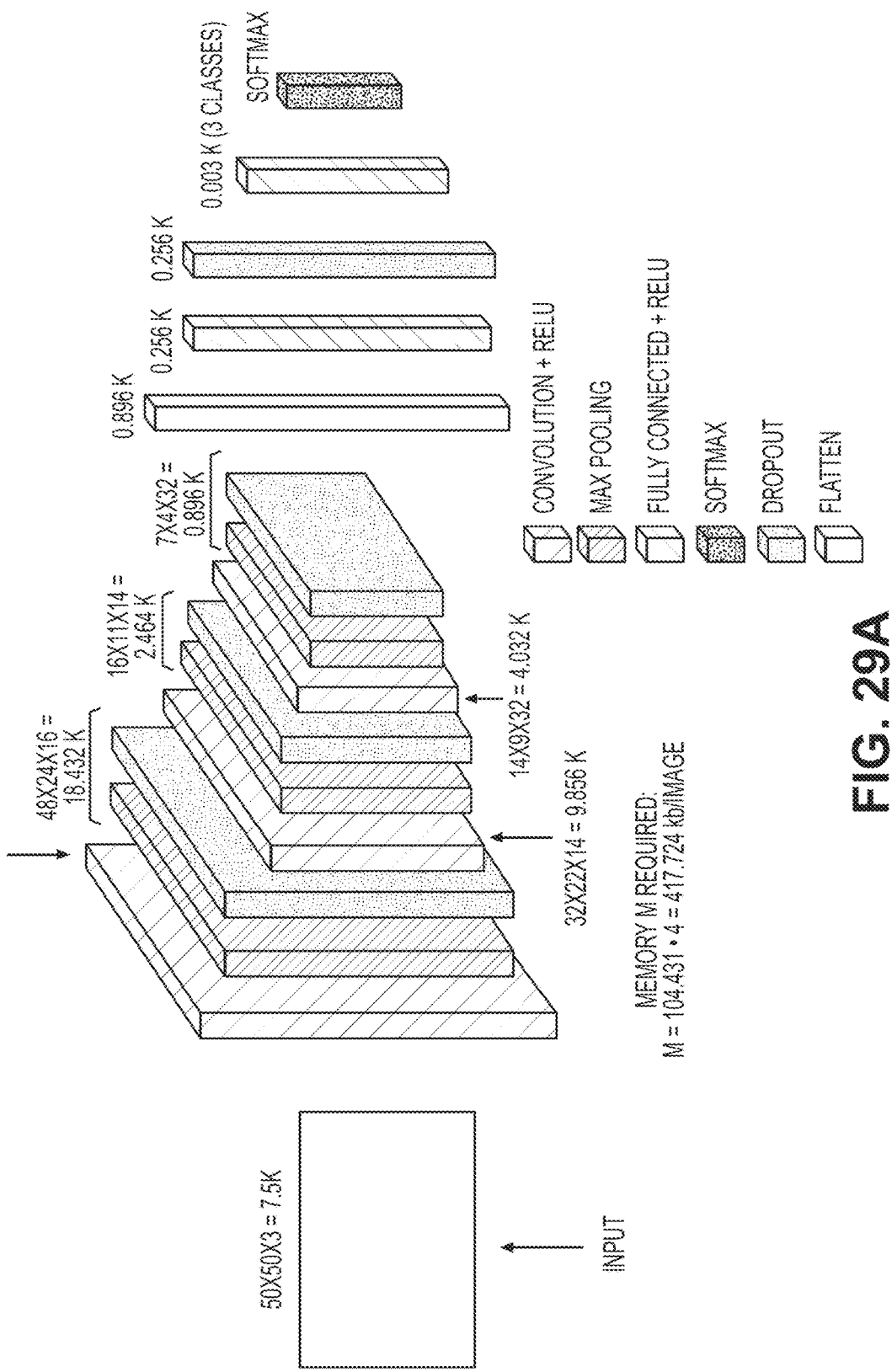
FIGS. 29A-29B illustrate an artificial intelligence architecture, according to some aspects of the present disclosure.
Figure 29B:
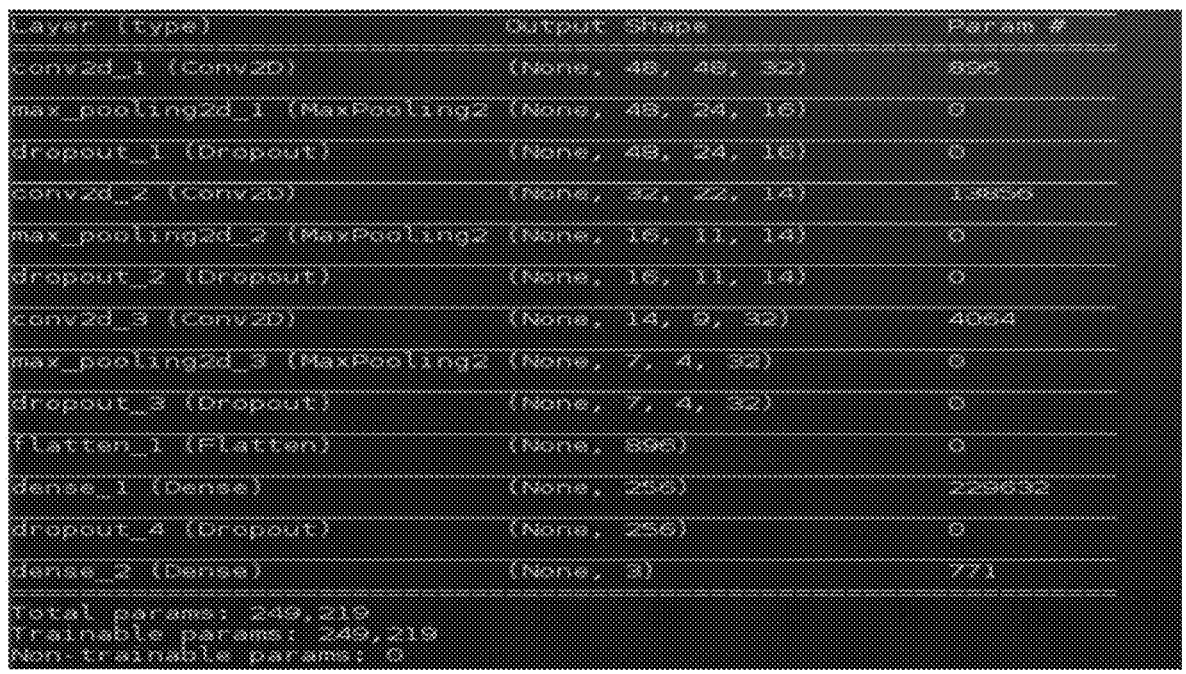
Figure 30A:
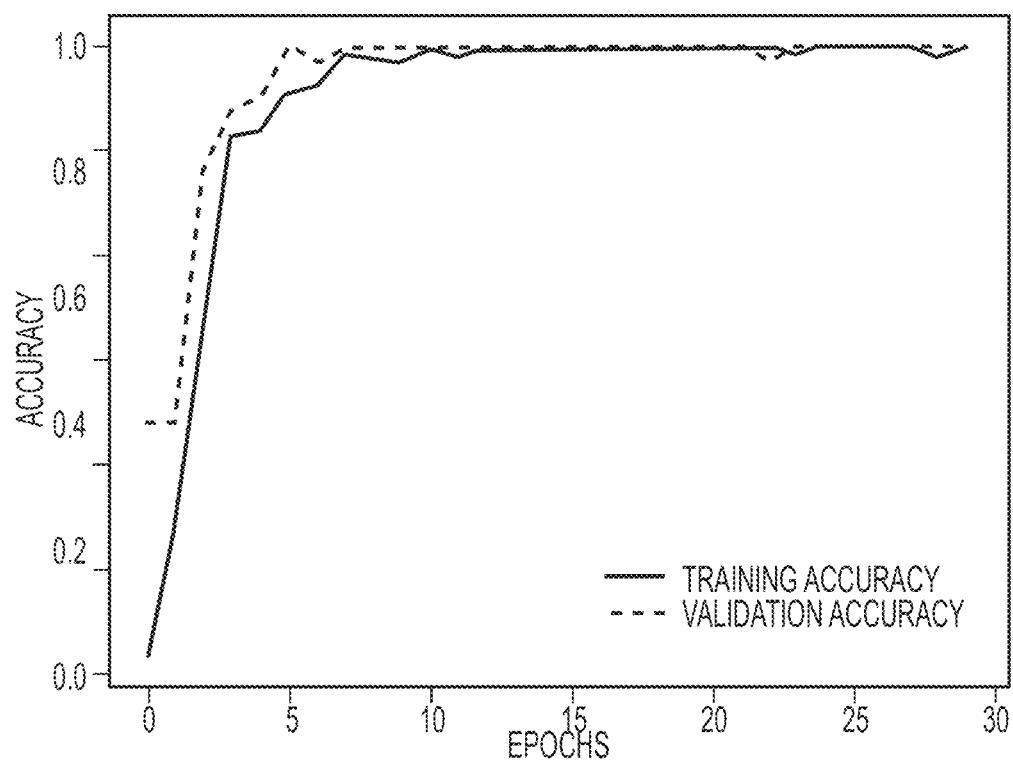
FIGS. 30A-30B illustrate training accuracy, validation accuracy, training loss, and validation loss curves for an artificial intelligence system, according to some aspects of the present disclosure.
Figure 30B:
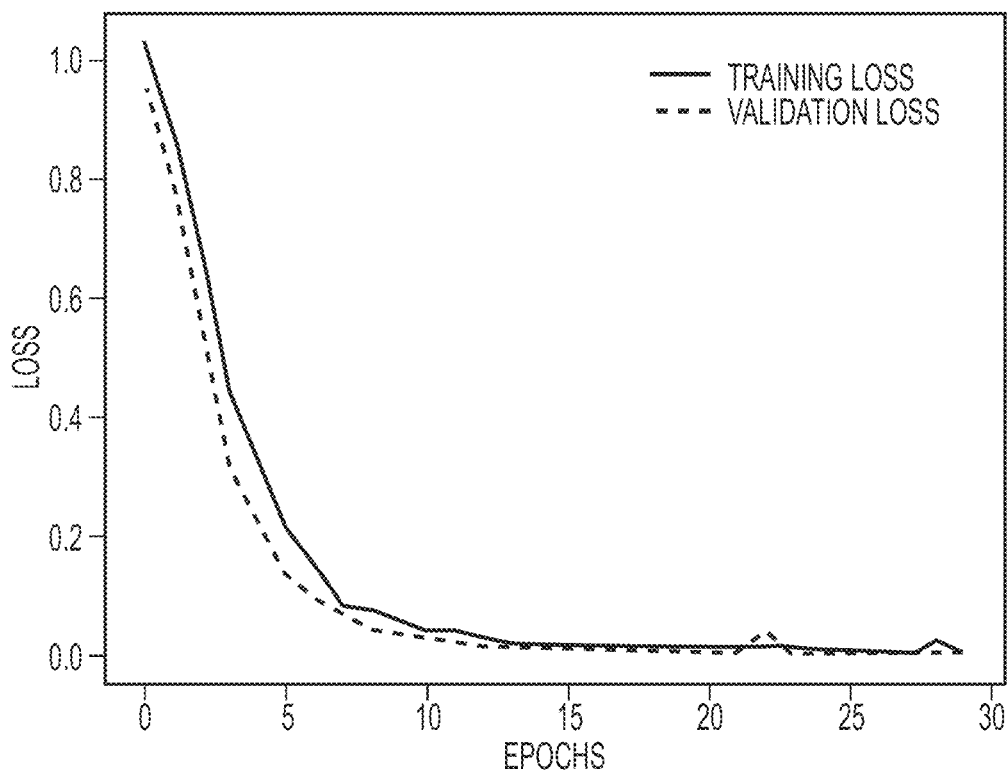

FIG. 18A illustrates a three-dimensional graph of variation of distance (vertical axis) between a real ultrasound image and a mathematical simulation with different parameters (horizontal axes) of a mathematical model for the surface of an implant, such as the surface model discussed hereinabove. The section of the graph in FIG. 18A where the distance is almost zero represents a match between the real ultrasound image and the mathematical simulation of the surface of the implant. FIG. 18B illustrates a graph showing the variation of distance (vertical axis) between a real ultrasound image and a mathematical simulation with different parameters (horizontal axes) of a snowstorm mathematical model, such as the snowstorm mathematical discussed hereinabove. In FIG. 18B, several sections of the graph indicate a distance of almost zero between the mathematical model and the real ultrasound image. Each of the graphs shown in FIGS. 18A and 18B illustrate how a mathematical model can be analyzed relative to a real ultrasound image.

In some examples, the system may utilize the above-described artificial neural networks and mathematical models in a program that assist with the visualization and analysis of medical implants. In some examples, the system may receive one or more ultrasound images and analyze the image(s) using one or more mathematical models. The analysis may employ artificial intelligence based on patient data (e.g., ultrasound images collected for patients experiencing implant failures). The system may include a database of ultrasound images as discussed above that are used to analyze images input into the system. The system may compare the input image(s) to the database of images as part of the analysis, and output irregularities detected by the system. For example, the output may include identification of a granuloma.

Figure 17:
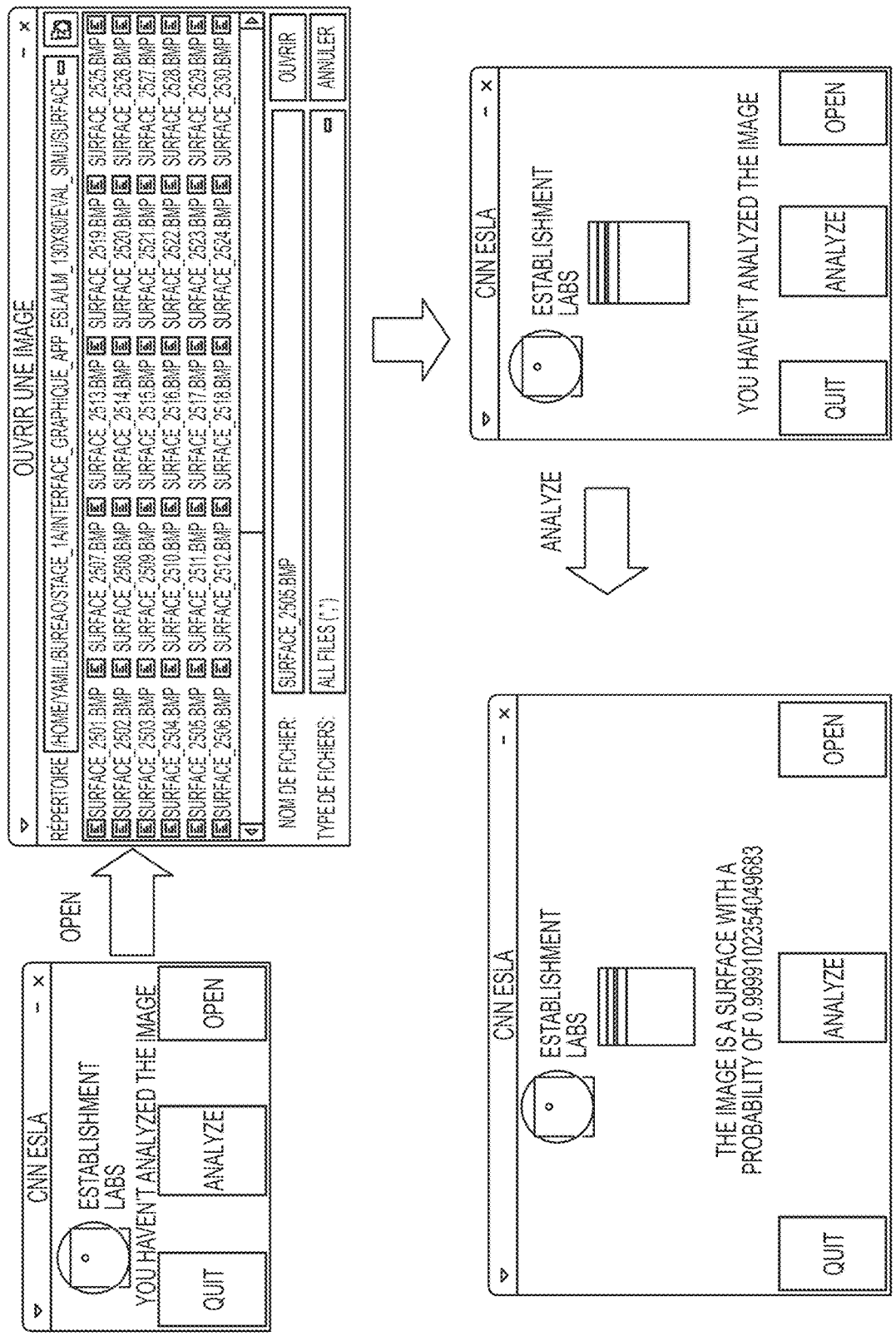
FIG. 17 illustrates a user interface of a system, according to some aspects of the present disclosure.

FIG. 17 illustrates an example of a system and user interface for analyzing ultrasound images of medical implants. The program may allow a user to select one or more images to upload for analysis. By selecting "Analyze," the user may initiate a series of algorithms as described above to assess the images and to have images that have been opened in the program to be analyzed, and may allow the user to select "Quit" to close the program. Once a user has selected images for the program to analyze and selected the icon "Analyze," the program may output the images opened within the program with indications in each of the images of a probability of one or more features present within the image, such as an implant surface or a rupture in an implant.

Figure 15:
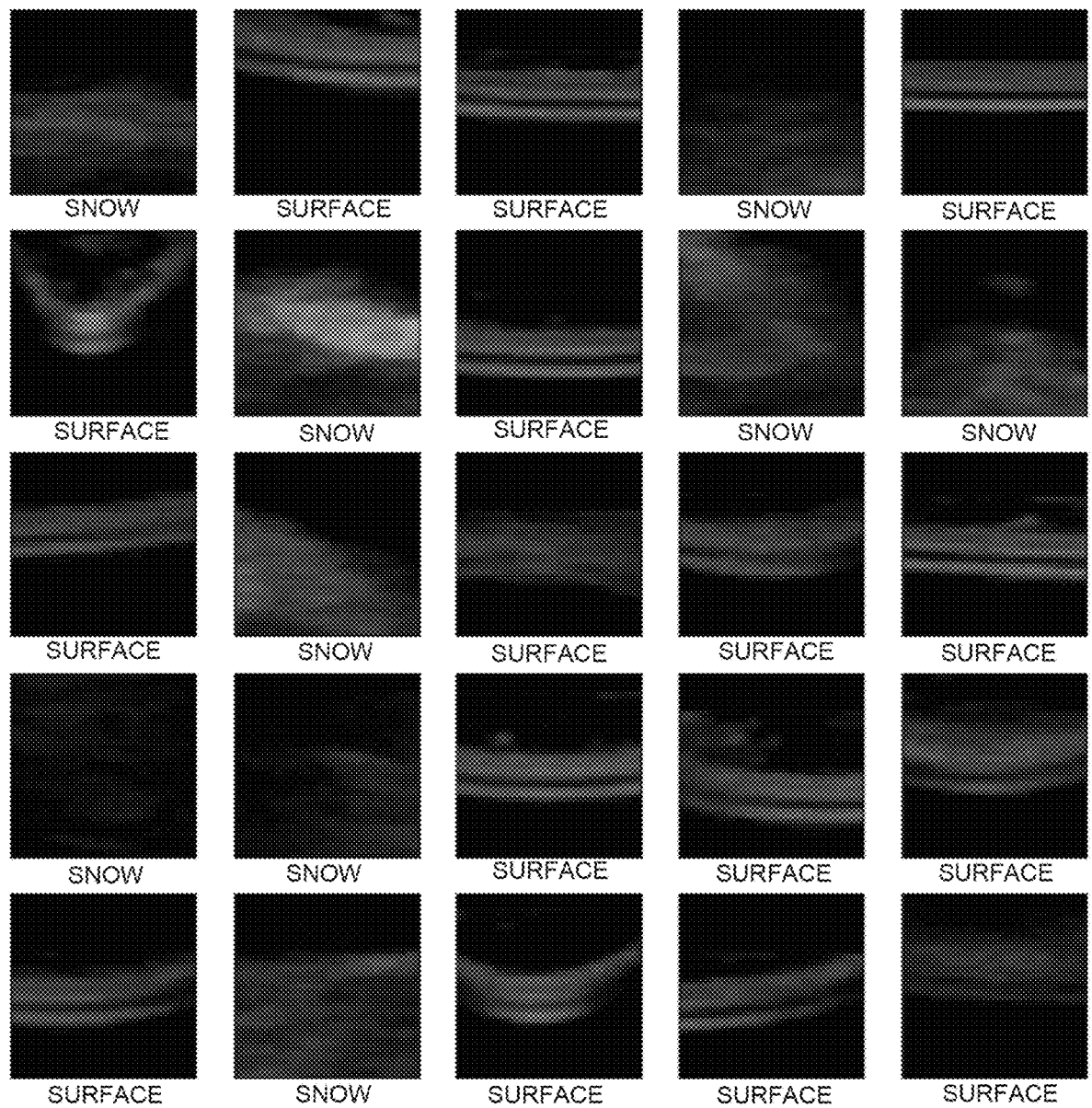
FIG. 15 illustrates an output of a software system program, according to some aspects of the present disclosure.
Figure 16:
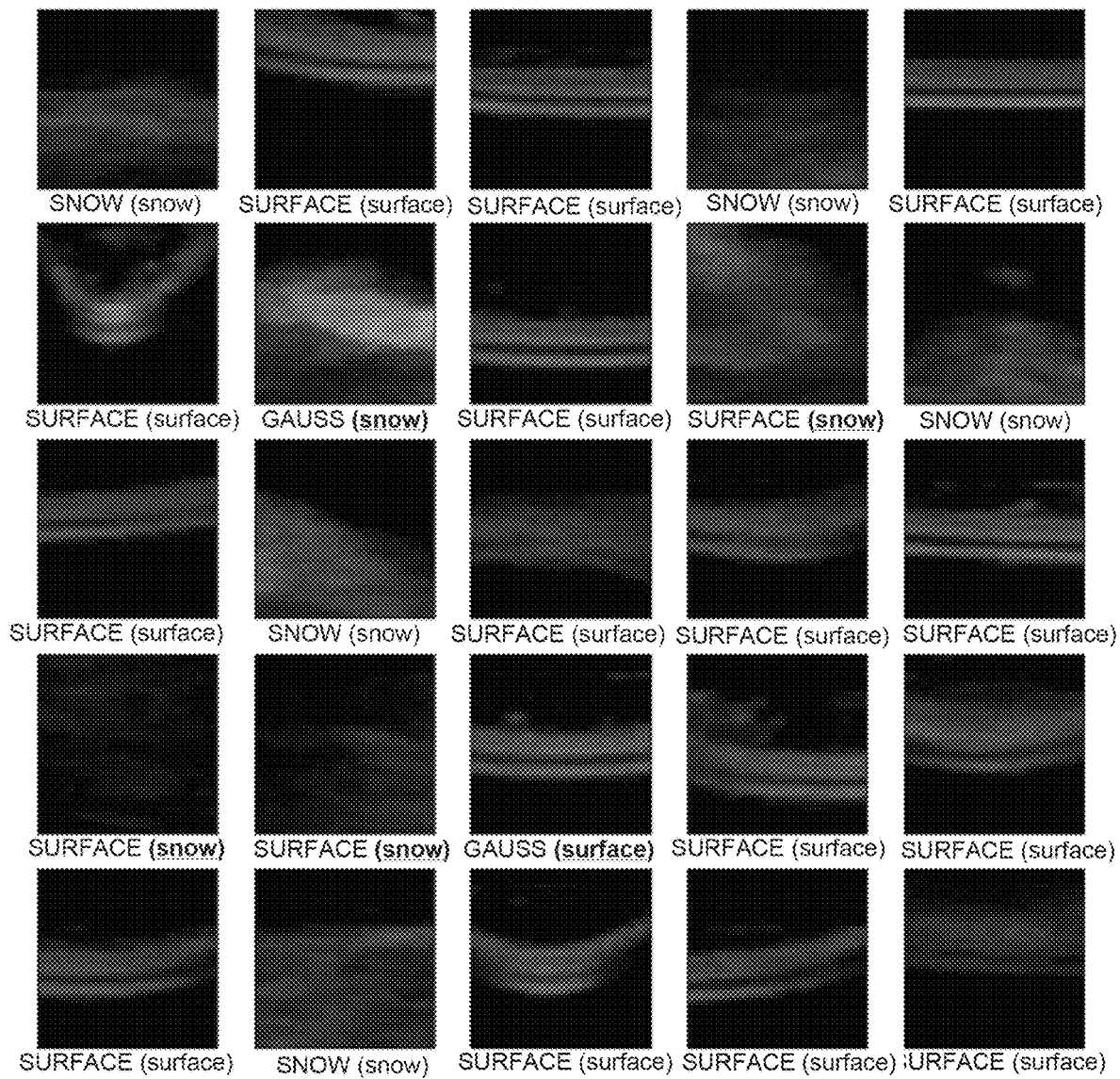
FIG. 16 illustrates an output of a system, according to some aspects of the present disclosure.

FIG. 15 illustrates a plurality of ultrasound images have been inputted into the system. The system algorithms have identified various features in the images, such as a surface of an implant. A medical professional may then examine the images and verify or correct the system's prediction of the features shown in each image. For example, a medical professional may be asked to indicate whether the system's prediction is believed to be correct by making a "correct" or "incorrect" selection (e.g., via a button or other user interface) on a display. FIG. 16 illustrates an output of the system with the system predictions and the correct features shown in parenthesis shown next to the predictions (35 of 40 predictions being correct in FIG. 16). A medical professional may mark the images as correct or incorrect, and upload the results to a database for the software system program to access in the future to calculate improved predictions.

Figures 13A, 13B:
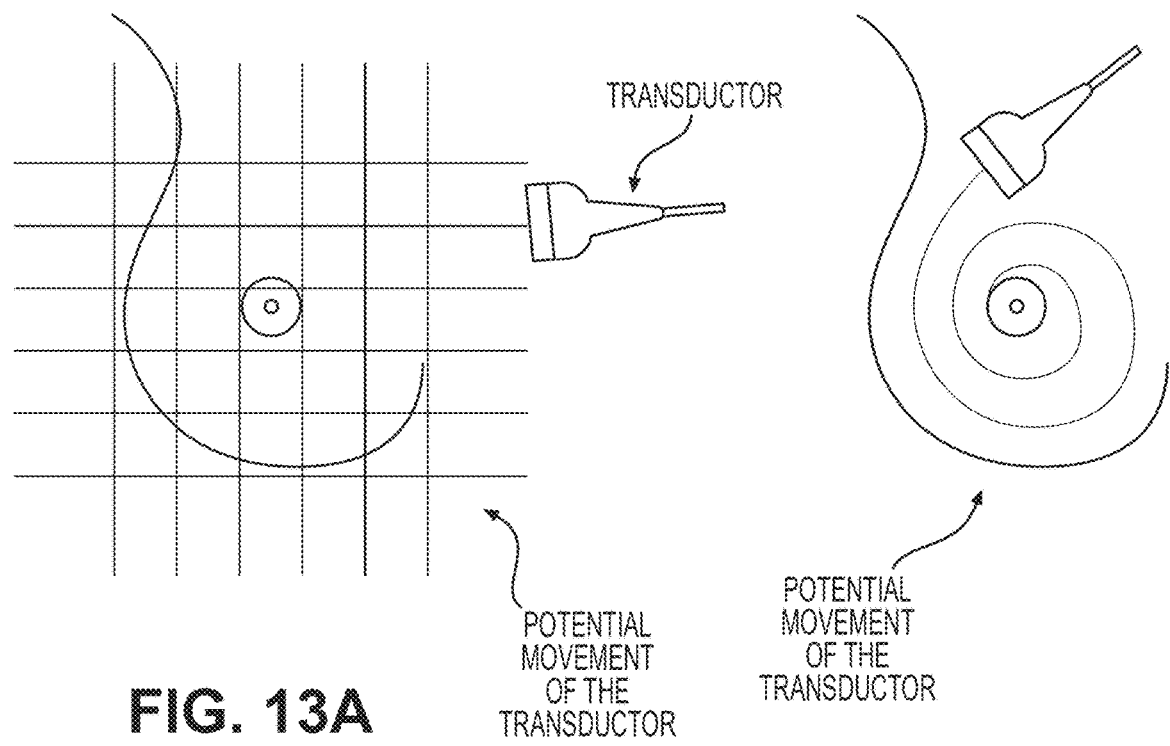
FIGS. 13A-13B illustrate patterns of movement for a transducer, according to some aspects of the present disclosure.

In some examples, the method of analysis may include obtaining ultrasound images with a transducer. FIGS. 13A-13B show an example of a pattern of movement (illustrated as a circular path in FIG. 13B) of a transducer that may be employed by a medical professional. Following a designated path of movement of the transducer when collecting ultrasound images for analysis may provide for improved results, e.g., wherein the system may analyze images obtained from various perspectives around the implant to better assess the integrity of the implant as a whole.

The systems herein may be configured to output a three-dimensional reconstruction of a patient's anatomy that includes an implant, e.g., based on ultrasound images. In some aspects, the system may include position sensors that may allow the system to tridimensionally reconstruct an implant based on the spatial coordinates measured using position sensors. In some examples, the system may output a three-dimensional virtual image of the surface of a patient's implant based on analysis of a collection of ultrasound images. The three-dimensional virtual image may identify areas of the implant that include irregularities, abnormalities, or other areas of concern, e.g., for further analysis by a medical professional.

FIG. 19 illustrates an example of a system for detecting ruptures and other irregularities in an implant using ultrasound images. For example, a user may upload an ultrasound image to an expert system (artificial intelligence). The expert system may include a cloud database of real and/or sample ultrasound images, a processor or processing system, and one or more mathematical models for intact (e.g., "normal") implants, ruptures, and intracapsular and/or extracapsular irregularities. The expert system may output results of analyzing the uploaded image to detect ruptures and/or other irregularities in an implant, and display the results to the user.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the present disclosure is not to be considered as limited by the foregoing description.

What is claimed is:

1. A computer-implemented method of processing images to determine integrity of an implant, the method comprising:
 receiving an ultrasound image of the implant in a body of a subject;
 converting the ultrasound image to at least one first sine-function;
  wherein oscillations and periods of the at least one first sine-function describes at least a portion of a surface of the implant;
 determining, based on the at least one first sine-function, one or more characteristics of a surface of the implant based on an intensity of pixels according to greyscale range of the ultrasound image;
 identifying an irregularity in the implant;
 converting the irregularity into a gauss function;
 generating a predicted status of the implant based on the one or more characteristics by comparison of the one or more characteristics with a database of image data; and
 displaying the predicted status of the implant.

2. The computer-implemented method of claim 1, wherein the implant is a breast implant.

3. The computer-implemented method of claim 1, wherein the database of image data includes a plurality of breast implant ultrasound images exhibiting extracapsular ruptures, contractures, and combinations thereof.

4. The computer-implemented method of claim 1, wherein the database of image data includes at least 50,000 images.

5. The computer-implemented method of claim 1, wherein the database of image data includes simulated or real images exhibiting echo lines, a snowstorm feature, or a combination thereof.

6. The computer-implemented method of claim 1, wherein determining the one or more characteristics includes determining a spatial period of consecutive echogenic lines.

7. The computer-implemented method of claim 1, wherein determining the one or more characteristics includes calculating a change in the greyscale intensity of pixels in a vertical direction of the ultrasound image.

8. The computer-implemented method of claim 1, wherein determining the one or more characteristics includes identifying echo lines, a snowstorm feature, or a combination thereof in the ultrasound image.

9. The computer-implemented method of claim 8, wherein determining the one or more characteristics includes distinguishing a snowstorm indicative of extracapsular rupture from a noise snowstorm.

10. The computer-implemented method of claim 1, wherein the method further comprises calculating a probability of implant failure based on the determined one or more characteristics, and displaying the predicted status of the implant includes displaying the probability.

11. The computer-implemented method of claim 1, wherein generating the predicted status of the implant is performed by an artificial neural network.

12. A system for processing images to determine integrity of an implant, the system comprising:
- at least one data storage device storing instructions for processing images to determine integrity of an implant; and
- at least one processor configured to execute the instructions to perform a method comprising:
  - receiving an ultrasound image of an implant in a body of a subject;
  - determining one or more characteristics of a surface of the implant based on a greyscale intensity of pixels of the ultrasound image;
    - wherein the at least one processor uses at least one sine function and at least one gauss function to describe the one or more characteristics of the implant;
    - wherein the at least one gauss function describes an irregularity in the surface the implant;
  - generating a predicted status of the implant based on the one or more characteristics by comparison of the one or more characteristics with a database of image data; and
  - displaying the predicted status of the implant.

13. The system of claim 12, wherein the at least one data storage device comprises the database of image data.

14. The system of claim 12, wherein the database of image data includes at least 50,000 images.

15. The system of claim 12, wherein the database of image data includes simulated or real images exhibiting echo lines, a snowstorm feature, or a combination thereof.

16. The system of claim 12, wherein the database of image data includes a plurality of breast implant ultrasound images exhibiting extracapsular ruptures, contractures, and combinations thereof.

17. A non-transitory computer-readable medium storing instructions that, when executed by a processor, cause the processor to perform a method for processing images to determine integrity of an implant, the method including:
- receiving an ultrasound image of an implant in a body of a subject;
- determining one or more characteristics of tissues surrounding the implant based on a greyscale intensity of pixels of the ultrasound image;
- converting the characteristics of tissues surrounding the implant into at least one first sine function;
- determining one or more characteristics of a surface of the implant based on the greyscale intensity of pixels of the ultrasound image;
  - wherein the greyscale intensity of pixels corresponding to the surface of the implant is converted into at least one second sine function;
- generating a predicted status of the implant based on the one or more characteristics of the tissues surrounding the implant and the one or more characteristics of the surface of the implant by comparing distances between at least one mathematically modeled image feature of the one or more characteristics in a database of image data and the one or more characteristics of the ultrasound image; and
- displaying the predicted status of the implant.

18. The non-transitory computer-readable medium of claim 17, wherein determining the one or more characteristics includes calculating a change in the greyscale intensity of pixels in a vertical direction of the ultrasound image.

19. The non-transitory computer-readable medium of claim 17, wherein determining the one or more characteristics includes distinguishing a snowstorm indicative of extracapsular rupture from a noise snowstorm.

20. The non-transitory computer-readable medium of claim 17, wherein the method further comprises calculating a probability of implant failure based on the determined one or more characteristics.

* * * * *